(12) United States Patent
Casavant et al.

(10) Patent No.: US 7,953,488 B2
(45) Date of Patent: May 31, 2011

(54) PRE-QUALIFICATION OF AN ALTERNATE SENSING CONFIGURATION

(75) Inventors: David Casavant, Reading, MA (US); Catherine R. Condie, Shoreview, MN (US); Jon W. Spence, Chisago City, MN (US); Nathan Munsterman, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 400 days.

(21) Appl. No.: 12/183,971

(22) Filed: Jul. 31, 2008

(65) Prior Publication Data

US 2010/0030289 A1 Feb. 4, 2010

(51) Int. Cl.
*A61N 1/00* (2006.01)
(52) U.S. Cl. .......................................... 607/27
(58) Field of Classification Search ................. 607/9, 27
See application file for complete search history.

(56) References Cited

U.S. PATENT DOCUMENTS

| | | |
|---|---|---|
| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,201,865 A | 4/1993 | Kuehn |
| 5,215,081 A | 6/1993 | Ostroff |
| 5,224,475 A | 7/1993 | Berg et al. |
| 5,226,415 A | 7/1993 | Girodo et al. |
| 5,292,343 A | 3/1994 | Blanchette et al. |
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,381,803 A | 1/1995 | Herleikson et al. |

(Continued)

OTHER PUBLICATIONS

Reply to Written Opinion from corresponding PCT Application Serial No. PCT/US2008/009241 filed Apr. 27, 2010 (12 pages).

(Continued)

*Primary Examiner* — George Manuel
(74) *Attorney, Agent, or Firm* — Michael C. Soldner

(57) ABSTRACT

Multiple sensing configurations may be qualified based on one induced tachyarrhythmia, e.g., ventricular fibrillation, or other qualification event during an implantation procedure. Each sensing configuration comprises a different combination of two or more electrodes used for sensing electrical signals of the heart of the patient. In some examples, an implantable medical device or other device generates qualification information for each sensing configuration, which may indicate whether the sensing configuration is qualified for subsequent cardiac event detection based on an accuracy of the cardiac event detection for the sensing configuration during the qualification event. One of the qualified configurations may initially be selected as a primary sensing configuration for subsequent cardiac event detection. Switching to an alternate sensing configuration, e.g., upon identification of any sensing integrity condition of the primary sensing configuration, may be expedited by the previous collection of qualification data for at least one other sensing configuration.

26 Claims, 13 Drawing Sheets

U.S. PATENT DOCUMENTS

| | | | |
|---|---|---|---|
| 5,383,909 A | 1/1995 | Keimel | |
| 5,411,530 A | 5/1995 | Akhtar | |
| 5,431,692 A | 7/1995 | Hansen et al. | |
| 5,462,060 A | 10/1995 | Jacobson et al. | |
| 5,507,746 A | 4/1996 | Lin | |
| 5,507,786 A | 4/1996 | Morgan et al. | |
| 5,534,018 A | 7/1996 | Wahlstrand et al. | |
| 5,545,183 A | 8/1996 | Altman | |
| 5,545,186 A | 8/1996 | Olson et al. | |
| 5,549,646 A | 8/1996 | Katz et al. | |
| 5,558,098 A | 9/1996 | Fain | |
| 5,564,434 A | 10/1996 | Halperin et al. | |
| 5,593,430 A * | 1/1997 | Renger | 607/18 |
| 5,660,183 A | 8/1997 | Chiang et al. | |
| 5,707,398 A | 1/1998 | Lu | |
| 5,722,997 A | 3/1998 | Nedungadi et al. | |
| 5,730,141 A | 3/1998 | Fain et al. | |
| 5,741,311 A | 4/1998 | Mc Venes et al. | |
| 5,755,735 A | 5/1998 | Richter et al. | |
| 5,755,736 A | 5/1998 | Gillberg et al. | |
| 5,755,742 A | 5/1998 | Schuelke et al. | |
| 5,776,168 A | 7/1998 | Gunderson | |
| 5,814,088 A | 9/1998 | Paul et al. | |
| 5,868,793 A | 2/1999 | Nitzsche et al. | |
| 5,891,170 A | 4/1999 | Nitzsche et al. | |
| 5,891,179 A | 4/1999 | Er et al. | |
| 5,897,577 A | 4/1999 | Cinbis et al. | |
| 5,910,156 A | 6/1999 | Cinbis et al. | |
| 5,944,746 A | 8/1999 | Kroll | |
| 6,067,473 A | 5/2000 | Greeninger et al. | |
| 6,070,097 A | 5/2000 | Kreger et al. | |
| 6,085,118 A | 7/2000 | Hirschberg et al. | |
| 6,112,119 A | 8/2000 | Schuelke et al. | |
| 6,129,746 A | 10/2000 | Levine et al. | |
| 6,141,585 A | 10/2000 | Prutchi et al. | |
| 6,155,267 A | 12/2000 | Nelson | |
| 6,169,923 B1 | 1/2001 | Kroll | |
| 6,266,554 B1 | 7/2001 | Hsu et al. | |
| 6,317,632 B1 | 11/2001 | Krig et al. | |
| 6,317,633 B1 | 11/2001 | Jorgenson et al. | |
| 6,434,428 B1 | 8/2002 | Sloman et al. | |
| 6,445,952 B1 | 9/2002 | Manrodt et al. | |
| 6,477,417 B1 | 11/2002 | Levine | |
| 6,493,586 B1 | 12/2002 | Stahmann et al. | |
| 6,629,931 B1 | 10/2003 | Begemann et al. | |
| 6,650,931 B1 | 11/2003 | McClure et al. | |
| 6,658,294 B1 | 12/2003 | Zadeh et al. | |
| 6,721,600 B2 | 4/2004 | Jorgenson et al. | |
| 6,760,624 B2 | 7/2004 | Anderson et al. | |
| 6,788,971 B1 | 9/2004 | Sloman et al. | |
| 6,865,141 B2 | 3/2005 | Tada et al. | |
| 7,047,083 B2 | 5/2006 | Gunderson et al. | |
| 7,167,747 B2 | 1/2007 | Gunderson et al. | |
| 7,236,828 B2 | 6/2007 | Casavant et al. | |
| 7,266,409 B2 | 9/2007 | Gunderson | |
| 7,289,851 B2 | 10/2007 | Gunderson et al. | |
| 7,333,855 B2 | 2/2008 | Gunderson et al. | |
| 7,369,893 B2 | 5/2008 | Gunderson | |
| 7,613,511 B2 * | 11/2009 | Wu et al. | 607/9 |
| 2001/0031997 A1 | 10/2001 | Lee | |
| 2001/0037366 A1 | 11/2001 | Webb et al. | |
| 2002/0091333 A1 | 7/2002 | Hsu et al. | |
| 2002/0116031 A1 | 8/2002 | Vonk | |
| 2002/0118215 A1 | 8/2002 | Ball et al. | |
| 2002/0120307 A1 | 8/2002 | Jorgenson et al. | |
| 2003/0074026 A1 | 4/2003 | Thompson et al. | |
| 2003/0204215 A1 | 10/2003 | Gunderson et al. | |
| 2004/0015197 A1 | 1/2004 | Gunderson | |
| 2004/0088018 A1 | 5/2004 | Sawchuk et al. | |
| 2004/0106955 A1 | 6/2004 | Swerdlow et al. | |
| 2004/0122487 A1 | 6/2004 | Hatlestad et al. | |
| 2004/0186388 A1 | 9/2004 | Gerasimov | |
| 2004/0220631 A1 | 11/2004 | Burnes et al. | |
| 2004/0230233 A1 | 11/2004 | Gunderson et al. | |
| 2004/0230242 A1 | 11/2004 | van Dam et al. | |
| 2005/0137636 A1 | 6/2005 | Gunderson et al. | |
| 2005/0154421 A1 | 7/2005 | Ousdigian | |
| 2005/0159785 A1 | 7/2005 | Rueter | |
| 2006/0074454 A1 | 4/2006 | Freeberg | |
| 2006/0224194 A1 | 10/2006 | Casavant et al. | |
| 2006/0235476 A1 | 10/2006 | Gunderson et al. | |
| 2007/0049982 A1 | 3/2007 | Cao et al. | |
| 2008/0082012 A1 | 4/2008 | Gunderson et al. | |
| 2008/0161872 A1 | 7/2008 | Gunderson | |

OTHER PUBLICATIONS

International Search Report and Written Opinion from corresponding PCT Application Serial No. PCT/US2008/009241 mailed Jun. 3, 2009 (9 pages).

International Preliminary Report on Patentability for PCT/US2008/009241, mail date Jun. 25, 2010 (10 pp).

* cited by examiner

PRE-QUALIFICATION OF AN ALTERNATE SENSING CONFIGURATION

TECHNICAL FIELD

The disclosure relates to implantable medical devices, and, more particularly, to configuration of implantable medical devices for sensing.

BACKGROUND

A wide variety of implantable medical devices for delivering a therapy or monitoring a physiological condition have been clinically implanted or proposed for clinical implantation in patients. Some implantable medical devices may employ one or more elongated electrical leads carrying stimulation electrodes, sense electrodes, and/or other sensors. Implantable medical devices may deliver electrical stimulation or fluid therapy to, and/or monitor conditions associated with, the heart, muscle, nerve, brain, stomach or other organs or tissue. Implantable medical leads may be configured to allow electrodes or sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry.

Some implantable medical devices, such as cardiac pacemakers or implantable cardioverter-defibrillators, provide therapeutic electrical stimulation to the heart via electrodes carried by one or more implantable leads. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting fibrillation.

Leads associated with an implantable medical device typically include a lead body containing one or more elongated electrical conductors that extend through the lead body from a connector assembly provided at a proximal lead end to one or more electrodes located at the distal lead end or elsewhere along the length of the lead body. The conductors connect stimulation and/or sensing circuitry within an associated implantable medical device housing to respective electrodes or sensors. Some electrodes may be used for both stimulation and sensing. Each electrical conductor is typically electrically isolated from other electrical conductors and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously disrupted. Connection mechanisms, such as set screws, may be insufficiently tightened at the time of implantation, followed by a gradual loosening of the connection. Also, lead pins may not be completely inserted. In some cases, changes in leads or connections may result in intermittent or continuous changes in lead impedance.

Short circuits, open circuits or significant changes in impedance may be referred to, in general, as lead related conditions. In the case of cardiac leads, sensing of an intrinsic heart rhythm through a lead can be altered by lead related conditions. Structural modifications to leads, conductors or electrodes may alter sensing integrity. Furthermore, impedance changes in the stimulation path due to lead related conditions may affect sensing and stimulation integrity for pacing, cardioversion, or defibrillation. In addition to lead related conditions, conditions associated with sensor devices or sensing circuitry, as well as conditions associated with electrodes or sensors not located on leads, may affect sensing integrity. Furthermore, T-wave oversensing, where the implantable medical device misidentifies T-waves as P- or R-waves, oversensing due to ambient radiofrequency noise, oversensing due to patient movement artifacts, or other over or undersensing issues, which may be unrelated to the integrity of implantable leads or other medical device components, may affect sensing integrity.

Implantable medical devices that deliver responsive therapies to treat arrhythmias, such as defibrillation, may be tested to determine whether they are able detect or diagnose the arrhythmia and deliver a responsive therapy that terminates the arrhythmia. Such testing, which may be referred to as qualification, may occur at the time the IMD is implanted. For example, during an implantation operation, ventricular fibrillation may be induced to determine whether the IMD is able to detect the fibrillation and deliver one or more responsive defibrillation shocks that terminate the fibrillation.

During qualification, the sensitivity of the IMD with regard to sensing may be altered to provide a margin of safety relative to the actual operating parameters of the device. Nevertheless, a subsequent lead related condition or other sensing integrity issue, i.e., that manifests some time after implantation and during chronic use of the IMD, may impair the ability of the IMD to sense tachyarrhythmias, or may cause the IMD to oversense tachyarrhythmias.

SUMMARY

In general, the disclosure is directed to techniques for qualifying multiple sensing configurations for a patient based on one induced tachyarrhythmia, e.g., ventricular fibrillation, or other qualification event. Each sensing configuration comprises a combination of two or more electrodes used for sensing electrical signals of the heart of the patient, and the multiple sensing configurations comprise different combinations of electrodes. The tachyarrhythmia induction or other qualification event may occur during implantation of an implantable medical device (IMD) within the patient. In the event of a sensing integrity issue with a primary sensing configuration, e.g., due to oversensing, undersensing, or a lead integrity issue, it may be desirable to switch to an alternate sensing configuration. The previous qualification of one or more other sensing configurations may allow the IMD to switch or be switched to an alternate sensing configuration without the need for an additional tachyarrhythmia induction for qualification of the alternate sensing configuration. Instead of or in addition to a tachyarrhythmia induction, a qualification event may include a sinus rhythm assessment in which the sensing configurations are evaluated for oversensing and/or undersensing during normal sinus rhythm of the patient.

The IMD or another device may generate qualification information for each of the sensing configurations that indicates an accuracy of the sensing configuration in detecting cardiac events during the qualification event. One of the qualified configurations may initially be selected as a primary sensing configuration for monitoring electrical signals of the heart, e.g., for detection of tachyarrhythmia events by an implantable medical device. The qualification information for one or more additional, e.g., potential alternate, configurations may be analyzed for pre-qualification at substantially the same time as the primary configuration, or stored for later retrieval and analysis, such as when a sensing integrity issue with the primary configuration is identified. The qualification information may be stored in a memory of the IMD, for example. The qualification of an alternate configuration, as well as the switching to an alternate configuration, may be automatic or user-directed.

In one example, the disclosure provides a method comprising receiving a plurality of sensed signals, each of the sensed signals sensed by a respective one of a plurality of sensing configurations during a qualification event, each of the sensing configurations comprising a respective one of a plurality of different combinations of two or more electrodes from a plurality of electrodes implanted within a patient. The method further comprises analyzing each of the sensed signals to detect cardiac events during the qualification event, and generating qualification information for each of the sensing configurations based on the analysis, the qualification information for each of the sensing configurations indicating whether the sensing configuration is qualified for subsequent cardiac event detection based on an accuracy of the cardiac event detection for the sensing configuration during the qualification event.

In another example, the disclosure provides a system comprising a plurality of electrodes implanted within a patient, an electrical sensing module that receives a plurality of sensed signals, each of the sensed signals sensed by a respective one of a plurality of sensing configurations during a qualification event, each of the sensing configurations comprising a respective one of a plurality of different combinations of two or more electrodes from the plurality of electrodes, and a processor that controls coupling of the sensing configurations to the electrical sensing module. At least one of the electrical sensing module and the processor analyzes each of the sensed signals to detect cardiac events during the qualification event. The processor generates qualification information for each of the sensing configurations based on the analysis, the qualification information for each of the sensing configurations indicating whether the sensing configuration is qualified for subsequent cardiac event detection based on an accuracy of the cardiac event detection for the sensing configuration during the qualification event.

In another example, a system comprises means for receiving a plurality of sensed signals, each of the sensed signals sensed by a respective one of a plurality of sensing configurations during a qualification event, each of the sensing configurations comprising a respective one of a plurality of different combinations of two or more electrodes from a plurality of electrodes implanted within a patient, means for analyzing each of the sensed signals to detect cardiac events during the qualification event, and means for generating qualification information for each of the sensing configurations based on the analysis, the qualification information for each of the sensing configurations indicating whether the sensing configuration is qualified for subsequent cardiac event detection based on an accuracy of the cardiac event detection for the sensing configuration during the qualification event.

The various techniques described in this disclosure may be capable of providing a number of advantages. In general, pre-qualification of one or more alternate sensing configurations allows a different sensing configuration to be used if a sensing integrity issue with the primary sensing configuration is identified. The pre-qualification may be advantageous in that the new sensing configuration has already been tested and confirmed to be adequate with respect to detection of cardiac events, and therefore another arrhythmia induction and qualification may not be required at the time of the sensing configuration switch.

In addition, multiple signal processing channels of a sensing module of the IMD may be utilized during the qualification event. In particular, each of the sensing configurations may be coupled to a respective channel during the qualification event. In this manner, the techniques and devices described by this disclosure may, for example, avoid the need for inducing multiple arrhythmias at the time of implantation of the IMD in order to qualify multiple sensing configurations at the time of implantation. Since the inducement of tachyarrhythmia may add stress to cardiac muscle and may place additional risk on the patient, the avoidance of multiple inducements is preferred.

DETAILED DESCRIPTION

Figure 1:
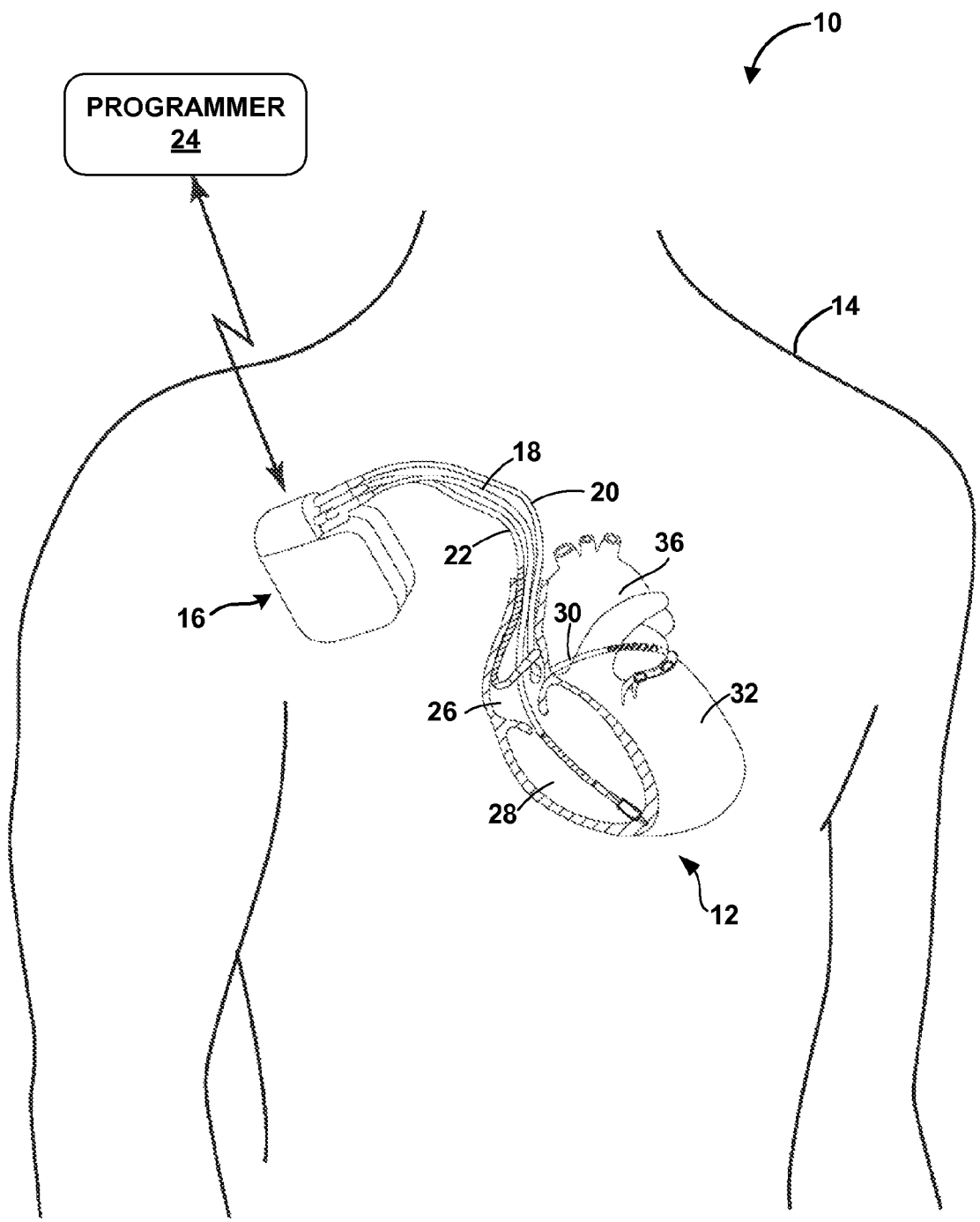
FIG. 1 is a conceptual diagram illustrating an example therapy system comprising an implantable medical device (IMD) for delivering stimulation therapy to a heart of a patient via implantable leads.

For detection and responsive treatment of tachyarrhythmias by an implantable medical device (IMD), a combination of two or more electrodes may be used to detect intrinsic signals indicative of heart wall depolarization. One or more of the electrodes may be located on implantable leads that extend from the IMD into the heart, to position the electrodes within or proximate to the heart. The IMD, which may also be referred to in some cases as an implantable cardioverter defibrillator (ICD), analyzes these intrinsic signals to, for example determine the frequency and/or magnitude of portions of the signal. For example, the IMD may analyze the signal to determine the frequency of P- or R-waves, which may be indicative of atrial or ventricular tachyarrhythmia, and deliver a therapy in response to detection of a tachyarrhythmia. The tachyarrhythmia may be, as examples, tachycardia or fibrillation. The responsive therapy may include one or more of pacing, cardioversion, or defibrillation pulses. In the case of fibrillation, P- or R-waves may alternatively be referred to as fib-waves.

The techniques described herein generally involve pre-qualifying multiple sensing configurations, e.g., during implantation of an implantable medical device (IMD). Each sensing configuration may comprise a combination of two or more electrodes used for sensing physiological signals within the patient, and the multiple sensing configurations comprise different combinations of electrodes. Although described hereinafter primarily with reference to detection of ventricular fibrillation based on R-R interval length, and delivery of responsive treatment in the form of defibrillation pulses, the techniques disclosed herein may be more broadly applicable to sensing configurations used for detecting any type of tachyarrhythmia, which may result in any type of responsive treatment, or modification of a more chronic treatment. Furthermore, the techniques of this disclosure are not limited to use in IMDs that detect or treat tachyarrhythmias, to IMDs that provide treatment, or even to implantable medical devices. Some or all of the techniques described herein may be implemented in any implantable or external medical device, or system comprising such a device.

During the course of chronic therapy provision monitoring, a sensing integrity issue may develop which results in inadequate sensing of the intrinsic signals from the heart. These sensing integrity issues may include oversensing that leads to false positive detections of atrial or ventricular contractions, or undersensing that leads to false negatives of atrial or ventricular contracts. In some cases, sensing integrity issues may be caused by lead integrity issues, such as broken or fractured conductors, degraded insulation, or inadequate connection between the a lead and IMD. In some cases, sensing integrity issues may be caused by ambient radiofrequency noise, or patient motion artifacts. In some cases, sensing may be impacted by changes in patient physiological condition due to disease, medication changes, or the like. When such sensing integrity issues or other sensing changes occur with a primary sensing configuration, it may be beneficial to be able to switch an alternate sensing configuration that may more accurately sense the intrinsic cardiac events, e.g., depolarizations.

Before an alternate sensing configuration can be used to sense intrinsic signals from the heart, it is generally desired to first test and qualify the sensing configuration. This qualification procedure for the primary sensing configuration is normally performed at IMD implantation by inducing ventricular fibrillation and determining if the primary sensing configuration successfully detected the ventricular fibrillation event. Since multiple ventricular fibrillation inducements, such as a first inducement at the time of implantation and a subsequent inducement to qualify an alternate sensing configuration at the time of a sensing integrity issue, are undesirable, this disclosure describes techniques by which multiple sensing configurations may be tested and pre-qualified from only one induced ventricular fibrillation, which may occur at the time of implantation.

Prior to the induced ventricular fibrillation, each of the sensing configurations is assigned to one of multiple detection channels, enabling qualification information to be generated for each sensing configuration during the ventricular fibrillation. The qualification information may indicate the ability of each sensing configuration to accurately detect cardiac events, and thereby detect the ventricular fibrillation. The qualification information may indicate which sensing configurations are pre-qualified to be later used during therapy if the initial primary sensing configuration experiences a sensing integrity issue or other sensing change. The qualification information may be stored within the IMD to allow for automatic or user-prompted switching to a pre-qualified, alternate sensing configuration.

FIG. 1 is a conceptual diagram illustrating an example therapy system 10 that may be used to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily, a human patient.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. In some alternative embodiments, therapy system 10 may include an additional lead or lead segment (not shown in FIG. 1) that deploys one or more electrodes within the vena cava or other vein. These electrodes may allow alternative electrical sensing configurations that may provide improved sensing accuracy in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect tachyarrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects tachycardia and fibrillation employing one or more tachycardia and fibrillation detection techniques known in the art.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16.

The user may use programmer 24 to program a therapy progression, select electrodes used to deliver cardioversion or defibrillation pulses, select waveforms for the cardioversion or defibrillation pulses, or select or configure a tachyarrhythmia detection algorithm for IMD 16. The user may also use programmer 24 to program aspects of other therapies provided by IMD 14, such as pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
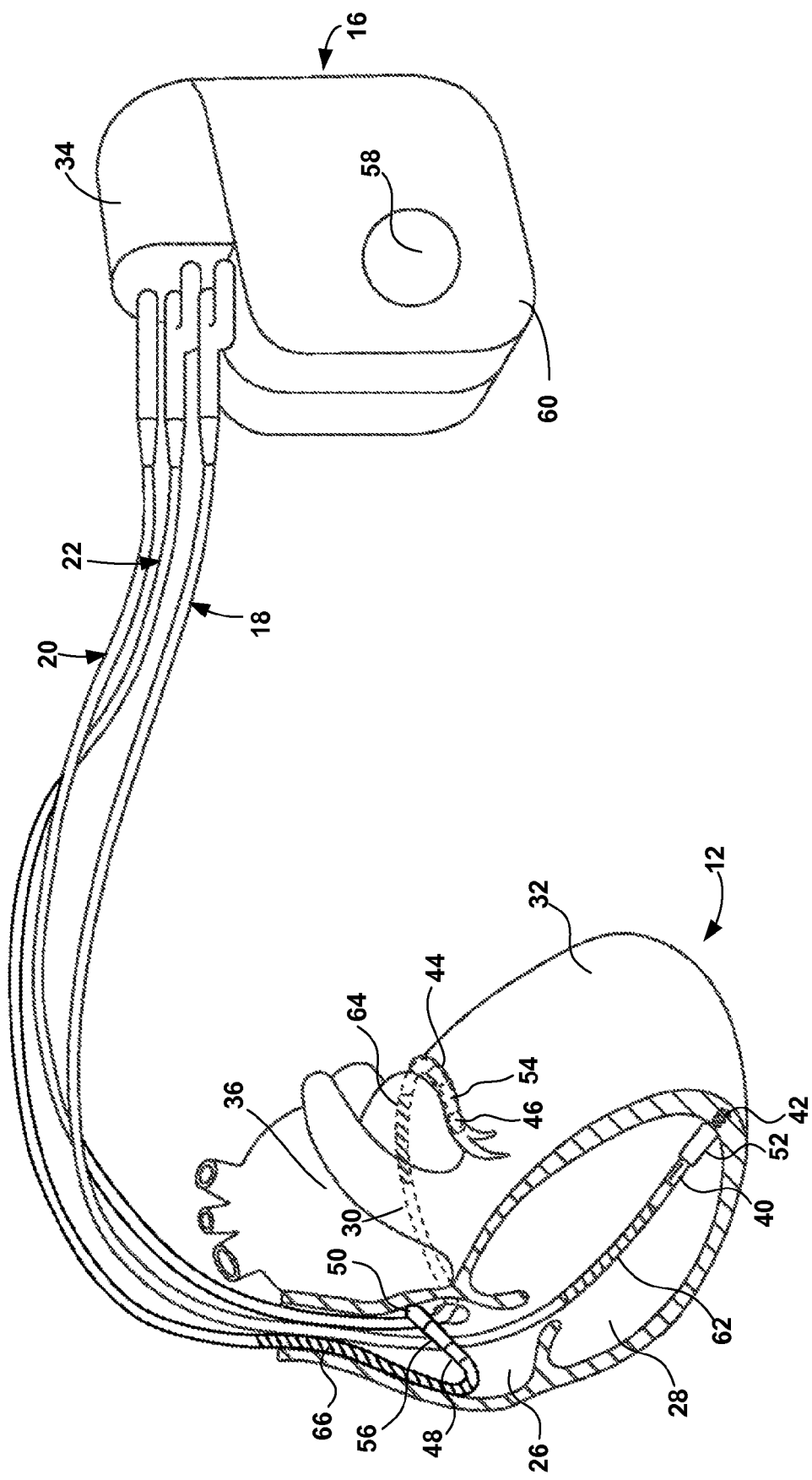
FIG. 2 is a conceptual diagram further illustrating the IMD and leads of the system of FIG. 1 in conjunction with the heart.

FIG. 2 is a conceptual diagram illustrating IMD 16 and leads 18, 20, and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36, but other embodiments may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58.

Any combination of two or more of electrodes 40, 42, 44, 46, 48, 50, 58, 62, 64 and 66 may be considered a sensing configuration. In some examples, a sensing configuration may be a bipolar electrode combination on the same lead, such as electrodes 40 and 42 of lead 18. On one lead having three electrodes, there may be at least three different sensing configurations available to IMD 16. These sensing configurations are, for the example of lead 18, tip electrode 42 and ring electrode 40, tip electrode 42 and elongated electrode 62, and ring electrode 40 and elongated electrode 62. However, some embodiments may utilize sensing configurations having electrodes of two different leads. Furthermore, a sensing configuration may utilize housing electrode 58 as one of the electrodes. In some examples, the sensing configuration may include electrodes disposed in or near the left ventricle or left atrium. Furthermore, pre-qualified sensing configurations may be a mathematical combination of traditional sensing vectors, each of which includes at least two electrodes, or a combination of a traditional sensing vector with the output of another sensor, e.g., a pressure sensor. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
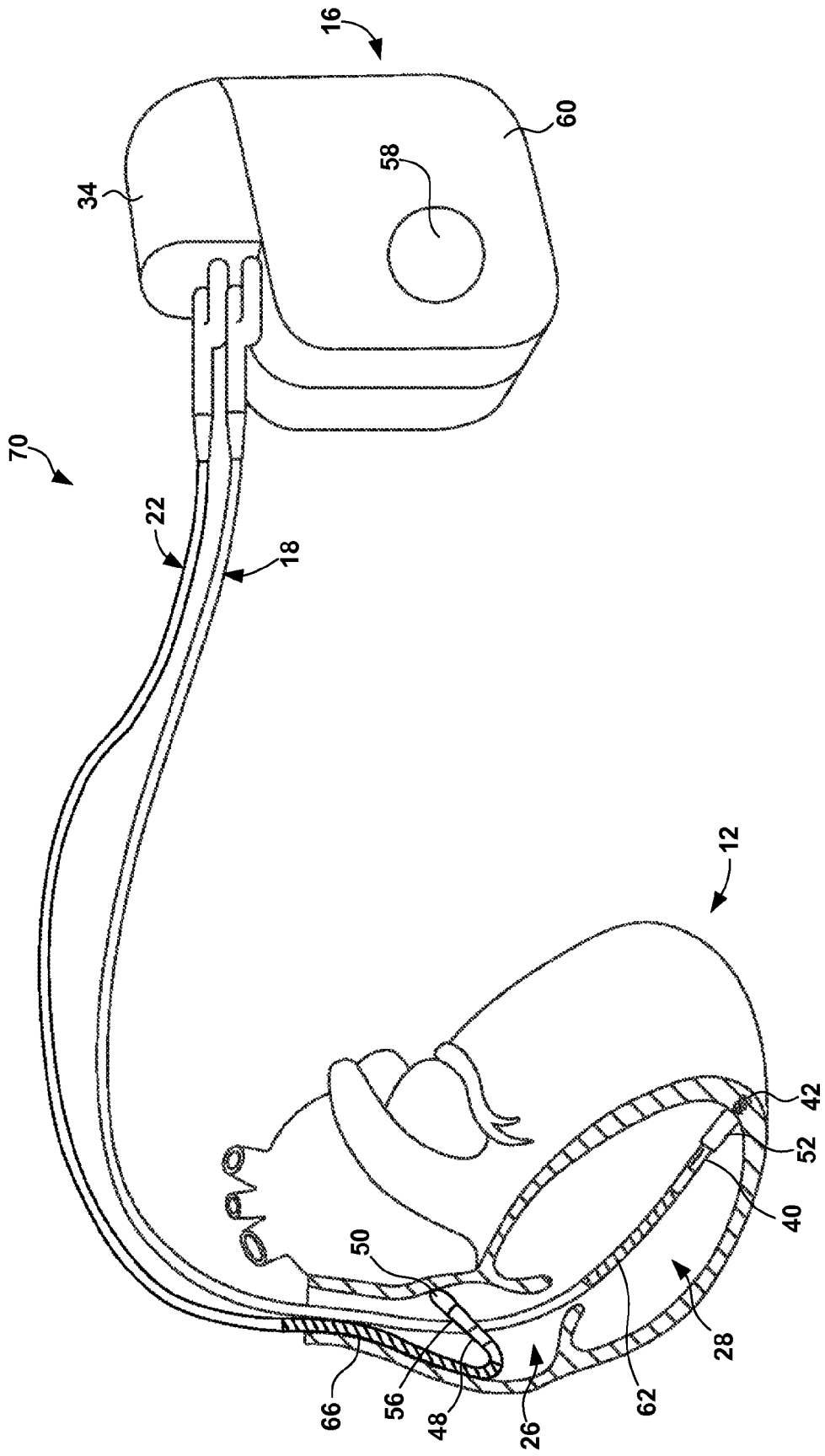
FIG. 3 is a conceptual diagram illustrating another example therapy system comprising an IMD for delivering stimulation therapy to a heart of a patient via leads.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used in sensing configurations that may be pre-qualified as described herein.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Although described primarily with respect to system 10, pre-qualification of sensing configurations as described herein may also be performed with respect to 70.

Figure 4:
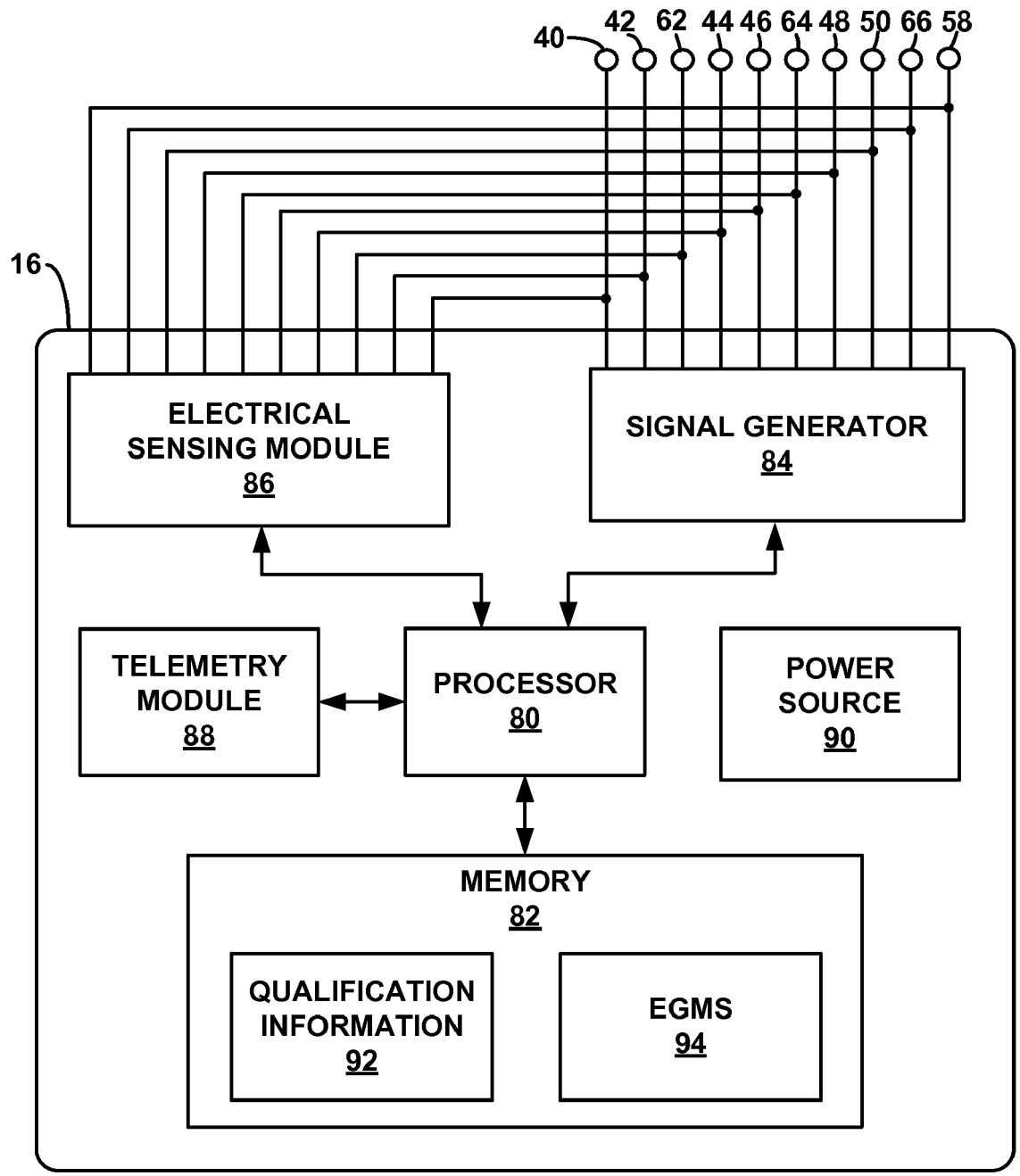
FIG. 4 is a functional block diagram illustrating an example configuration of the IMD of FIGS. 1 and 2.

FIG. 4 is a functional block diagram illustrating one example configuration of IMD 16, which includes processor 80, memory 82, signal generator 84, electrical sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. Specifically, processor 44 may control signal generator 84 to deliver electrical pulses with the amplitudes, pulse widths, frequency, or electrode polarities specified by the selected one or more therapy programs. Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16.

Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing configuration, via the switch module within electrical sensing module 86, e.g., by providing signals via a data/address bus. Electrical sensing module 86 includes multiple detection channels, each of which may comprise an amplifier. In another example, electrical sensing module may only include one detection channel to sensing cardiac signals that may then be digitized and processed by processor 80 to analyze the signal detected by multiple sensing configurations. In response to the signals from processor 80, the switch module of within electrical sensing module 86 may couple selected electrodes to one of the detection channels.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals electrical sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves with detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a tachyarrhythmia event, such as atrial or ventricular fibrillation or tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other tachyarrhythmia detection methodologies may also be employed by processor 80 in other examples.

In the event that processor 80 detects an atrial or ventricular tachyarrhythmia based on signals from electrical sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver cardioversion or defibrillation pulses to heart 12, signal generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of signal generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrogram signals) produced by atrial and ventricular sense amp circuits within electrical sensing module 86 to programmer 24. Programmer 24 may interrogate IMD 16 to receive the electrograms. Processor 80 may store electrograms (EGMS) 94 within memory 82, and retrieve stored electrograms 94 from memory 82. Processor 80 may also generate and store marker codes indicative of different cardiac events that electrical sensing module 86 detects, such as atrial and ventricular depolarizations, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Memory 82 may also store instructions that allow processor 80 to pre-qualify multiple sensing configurations, select an initial primary sensing configuration, and switch to an alternate sensing configuration when necessary to overcome any sensing problems with the primary sensing configuration. Upon implantation, memory 82 may store all possible sensing configurations based upon the number and type of leads coupled to IMD 16. According to this information, processor 80 may determine the multiple different sensing configurations to be pre-qualified and couple each sensing configuration to a different available detection channel in order to simultaneously qualify each sensing configuration from a single qualification event, e.g., induced ventricular fibrillation. In some examples, processor 80 receives a selection of the sensing configurations to be qualified from a user via telemetry module 88. The user may select the sensing configurations via programmer 24, or another computing device that is able to communicate with IMD 16 using any of the techniques mentioned herein or known in the art.

Processor 80 generates qualification information 92 for each sensing configuration. Qualification information 92 for a sensing configuration may indicate an accuracy of cardiac event detection using the sensing configuration. Qualification information 92 for a sensing configuration may indicate whether the sensing configuration is qualified for subsequent cardiac event detection, e.g., qualified for chronic cardiac event detection to control pacing or tachyarrhythmia therapies.

As an example, processor 80 may generate qualification information 92 based on an analysis of whether the sensing configuration did detect and facilitate, or would have properly detected and facilitated termination of the induced tachyarrhythmia. Qualification information 92 may include a simple qualified or not qualified indication, or terminated or not terminated (with respect to the induced tachyarrhythmia) indication. In other examples, qualification information 92 for a sensing configuration may include a marker channel for the sensing configuration. The marker channel may illustrate cardiac event detection via the sensing configuration, and may thereby indicate the accuracy of such cardiac event detection, e.g., whether there was oversensing or undersensing via the sensing configuration. The marker channel may also indicate when and how the induced tachyarrhythmia was or would have been terminated using the sensing configuration. In some examples, one of the plurality of sensing configurations qualified during the qualification event will be used by processor 80 to control the delivery of one or more defibrillation pulses in response to the induced fibrillation. Processor 80 may provide an indication of when or if defibrillation pulses would have been delivered in the marker channel for other sensing configurations.

As illustrated in FIG. 4, memory 82 may store qualification information 92. In other examples, qualification information 92 may additionally or alternatively be stored outside of IMD 16, such as within programmer 24 or on a remote server or database.

Processor 80 may select the initial primary sensing configuration from among the plurality of sensing configurations tested during the qualification event according to qualification information 92. In some examples, processor 80 may receive a selection of the primary sensing configuration from a user via telemetry module 88. Processor 80 may store qualification information 92 for one or more others of the plurality of sensing configurations that are possible alternate sensing configurations for later retrieval in the event that switching sensing configurations becomes necessary or desirable.

Processor 80 may monitor or periodically check the primary sensing configuration for sensing integrity issues. Upon any indication that the primary sensing configuration is oversensing cardiac signals, undersensing cardiac signals, or that there is a lead integrity issue, processor 80 may automatically retrieve qualification information 92 stored in memory 82 and switch to the next most accurate qualified sensing configuration as an alternate sensing configuration. In this manner, IMD 16 may be able to more quickly ameliorate any issue with the primary sensing configuration. In other examples, processor 80 may present qualification information 92 to a user, e.g., via telemetry module 88, and programmer 24 or another computing device, and receive selection or approval of an alternate sensing configuration. It should be noted that at any one or more decision points in determining which sensing configuration to use, a clinician or other user may make the selection or confirm a selection made by processor 80.

Processor 80 may monitor or periodically check for sensing integrity issues using any techniques known in the art, which may include periodic or triggered lead impedance measurements. For example, processor 80 may implement the techniques described in U.S. Pat. No. 7,289,851 to Gunderson et al., entitled "METHOD AND APPARATUS FOR IDENTIFYING LEAD-RELATED CONDITIONS USING IMPEDANCE TRENDS AND OVERSENSING CRITERIA," which issued on Oct. 30, 2007, and is incorporated herein by reference in its entirety. Instead of or in addition to lead impedance measurements, sensing integrity evaluation may include detection of non-physiological, e.g., short, R-R or P-P intervals, or detection of non-sustained tachyarrhythmias, as described in U.S. Pat. No. 7,289,851.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 5:
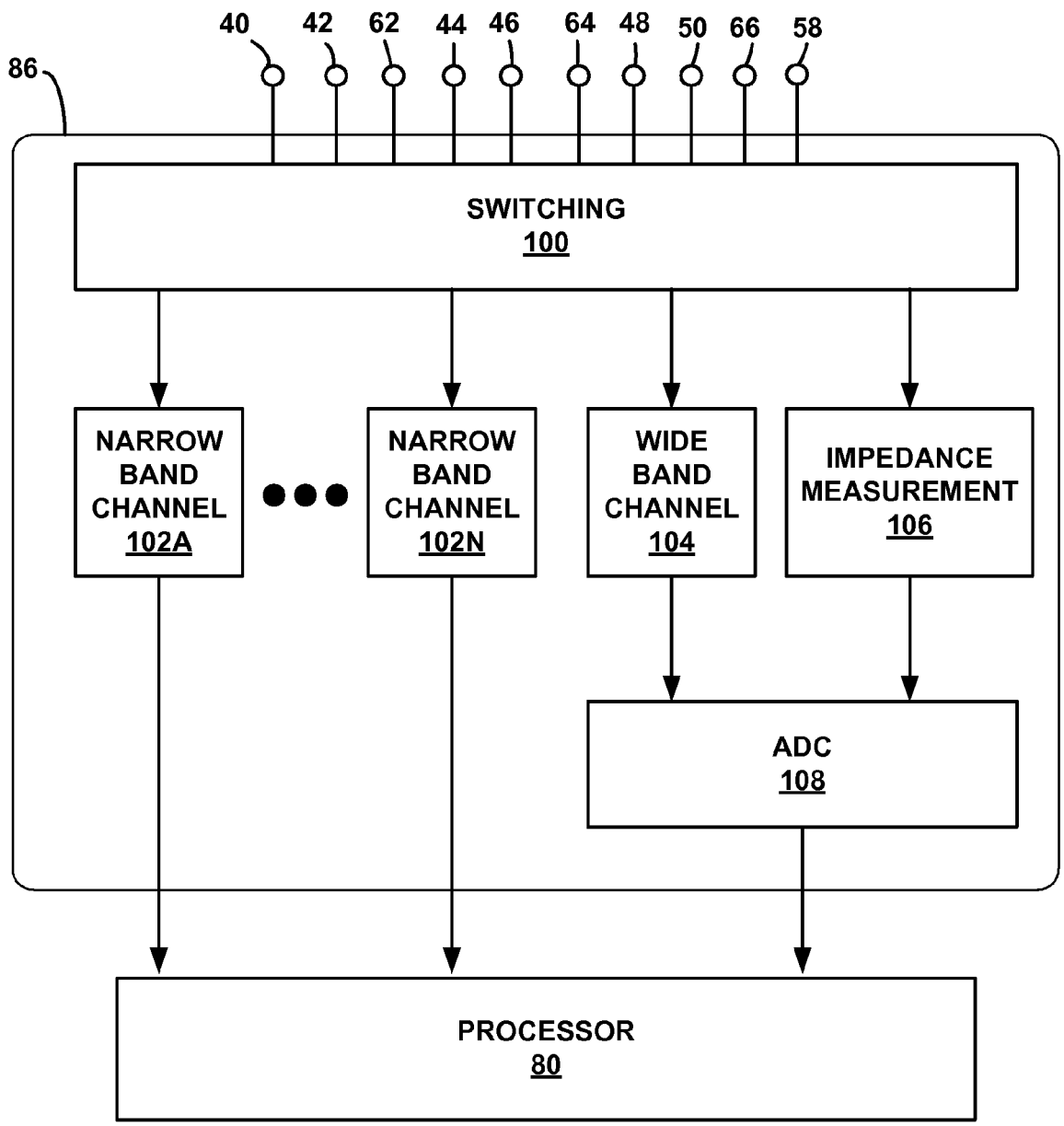
FIG. 5 is a functional block diagram illustrating an example electrical sensing module having multiple detection channels.

FIG. 5 is a block diagram of an example configuration of electrical sensing module 86. As shown in FIG. 5, electrical sensing module 86 includes multiple components including switching module 100, narrow band channels 102A to 102N, wide band channel 104, impedance measurement module 106, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 and impedance measurement module 106, at any given time. Switching module 100 may comprise a multiplexer, and in some examples may comprise a transistor array, an array of microelectromechanical switches, or the like.

Each of narrow band channels 102 may comprise a narrow band filtered sense-amplifier that compares the detected signal to a threshold. If the filtered and amplified signal is greater than the threshold, the narrow band channel indicates that a certain electrical heart event has occurred. Processor 80 then uses that detection in measuring frequencies of the detected events. Narrow band channels 102 may have distinct functions. For example, some various narrow band channels may be used to detect either atrial or ventricular events.

In one example, at least one narrow band channel 102 may include an R-wave amplifier that receives signals from the sensing configuration of electrodes 40 and 42, which are used for sensing and/or pacing in right ventricle 28 of heart 12. Another narrow band channel 102 may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Wide band channel 104 may comprise an amplifier with a relatively wider pass band than the R-wave or P-wave amplifiers. Signals from the selected sensing electrodes that are selected for coupling to this wide-band amplifier may be converted to multi-bit digital signals by ADC 108. In some examples, processor 80 may store signals the digitized versions of signals from wide band channel 104 in memory 82 as EGMs 94. In some examples, the storage of such EGMs 94 in memory 82 may be under the control of a direct memory access circuit.

In some examples, processor 80 may employ digital signal analysis techniques to characterize the digitized signals from wide band channel 104 to, for example detect and classify the patient's heart rhythm. Processor 80 may detect and classify the patient's heart rhythm by employing any of the numerous signal processing methodologies known in the art. Further, in some examples, processor 80 may analyze the morphology of the digitized signals from wide band channel 104 to distinguish between noise and cardiac depolarizations.

In some examples, as discussed above, processor 80 periodically checks or monitors the sensing integrity of the primary sensing configuration. In such examples, sensing module 86 and/or processor 80 may be capable of collecting, measuring, and/or calculating impedance data for any of a variety of electrical paths that include two or more of electrodes 40, 42, 44, 46, 48, 50, 58, 62, 64 and 66. Impedance measurement module 106 may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 106.

In some examples, processor 80 may perform an impedance measurement by controlling delivery, from signal generator 84, of a voltage pulse between first and second electrodes. Measurement module 106 may measure a resulting current, and processor 80 may calculate a resistance based upon the voltage amplitude of the pulse and the measured amplitude of the resulting current. In other examples, processor 80 may perform an impedance measurement by controlling delivery, from signal generator 84, of a current pulse between first and second electrodes. Measurement module 106 may measure a resulting voltage, and processor 80 may calculate a resistance based upon the current amplitude of the pulse and the measured amplitude of the resulting voltage. Measurement module 86 may include circuitry for measuring amplitudes of resulting currents or voltages, such as sample and hold circuitry.

In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In one embodiment, IMD 16 may analyze the measured impedance values, and may compare these values, or other computed values, to determined thresholds and identify any possible conditions with one or more electrical paths that include two or more of the electrodes. For example, IMD 16 may, as a result of one or more comparisons, determine that one or more of leads 18, 20, and 22 has a lead-related condition, or more specifically that one or more electrodes or associated conductors within the leads may have an integrity issue. IMD 16 may send impedance measurement and/or analysis data to programmer 24 via telemetry module 88.

Upon implantation of IMD 16 and leads 18, 20, 22, multiple sensing configurations may be pre-qualified for later use as a sensing configuration during therapy. At any given time, IMD 16 usually only uses one sensing configuration to sense cardiac events in a given chamber, such as one sensing configuration to detect depolarization and repolarization of the right ventricle. Before a sensing configuration can be used to sense cardiac events during therapy, the sensing configuration may need to be qualified to do so. Advantageously, according to the techniques described herein, multiple detection channels must be employed for qualifying multiple sensing configurations for detecting ventricular defibrillation during a single induced fibrillation, which may thereby avoid the need for more than one inducement of ventricular fibrillation to qualify more than one sensing configuration.

The multiple narrow band channels 102 may allow IMD 16 to qualify multiple sensing configurations. A first narrow band channel 102 may be normally used to detect ventricular fibrillation from the sensing configuration of bipolar electrodes 40 and 42 in the right ventricle. This sensing configuration of a tip electrode and ring electrode may be the preferred sensing configuration. Additionally, a second sensing configuration may be associated with another narrow band channel 102. The second sensing configuration may include electrodes 42 and 62. In this manner, processor 80 may generate qualification information 92 for two sensing configurations at the same time, e.g., based on the output of the narrow band channels 102.

The qualification information 92 may indicate whether the induced ventricular fibrillation was successfully detected with either or both of the sensing configurations. If both are successful, the qualification information 92 may identify the sensing configurations as pre-qualified sensing configurations. Processor 80 may then switch to the unused sensing configuration for ventricular sensing if any sensing problems arise with the use of the primary sensing configuration.

IMD 16 may have any number of narrow band channels 102. Generally, one sensing configuration may be pre-qualified by using one assigned narrow band channel. Therefore, more sensing configurations may be pre-qualified as long as there is another narrow band channel available to be assigned to detect the signals from the sensing configuration. If possible, it may be beneficial to pre-qualify as many sensing configurations as reasonable or possible in order to have alternate sensing configurations pre-qualified and available during therapy if needed.

In addition, electrical sensing module 86 may include a detection channel comprising wide band channel 104. Instead of, or in addition to, narrow band channels 102, wide band channel 104 may be used to pre-qualify one or more sensing configurations. After passing though wide band channel 104, a resulting signal may be digitized by ADC 108 before being processed by processor 80 and/or stored in memory 82 as an EGM 94. Processor 80 may employ digital signal analysis techniques to detect cardiac events that occurred during the qualification event based on the digital signal. The analysis of the sensed signals by narrow band channels 102 to detect cardiac events may be substantially in real-time, while the analysis of the digitized signal by processor 80 may be post-processed at any time after the qualification event. Although pre-qualification of sensing configurations using one or more wide-band channels 104 and post-processing by processor 80 may be processing intensive as compared to using a narrow band channel 102, it may allow for one or more additional sensing configurations to be pre-qualified. In one example, processor 80 may process one channel in real-time while processor 80 or another processor processes additional channels, whether received from narrow-band channels 102 or wide-band channels 104, at a later time to pre-qualify multiple sensing configurations.

Qualification of sensing configurations may be performed with narrow band channels 102 configured with a sensitivity of 1.2 mV. Similarly, any post processing by processor 80 may be configured to reflect this sensitivity. This sensitivity is four times greater than the usually programmed sensitivity of 0.3 mV to build in the appropriate safety margin. Therefore, if a sensing configuration cannot detect the ventricular fibrillation under the decreased sensitivity during pre-qualification, that sensing configuration will likely not be pre-qualified to be used during therapy. In general, the safety margin tested during pre-qualification may be any margin greater than that used during normal therapeutic detection.

Figure 6:
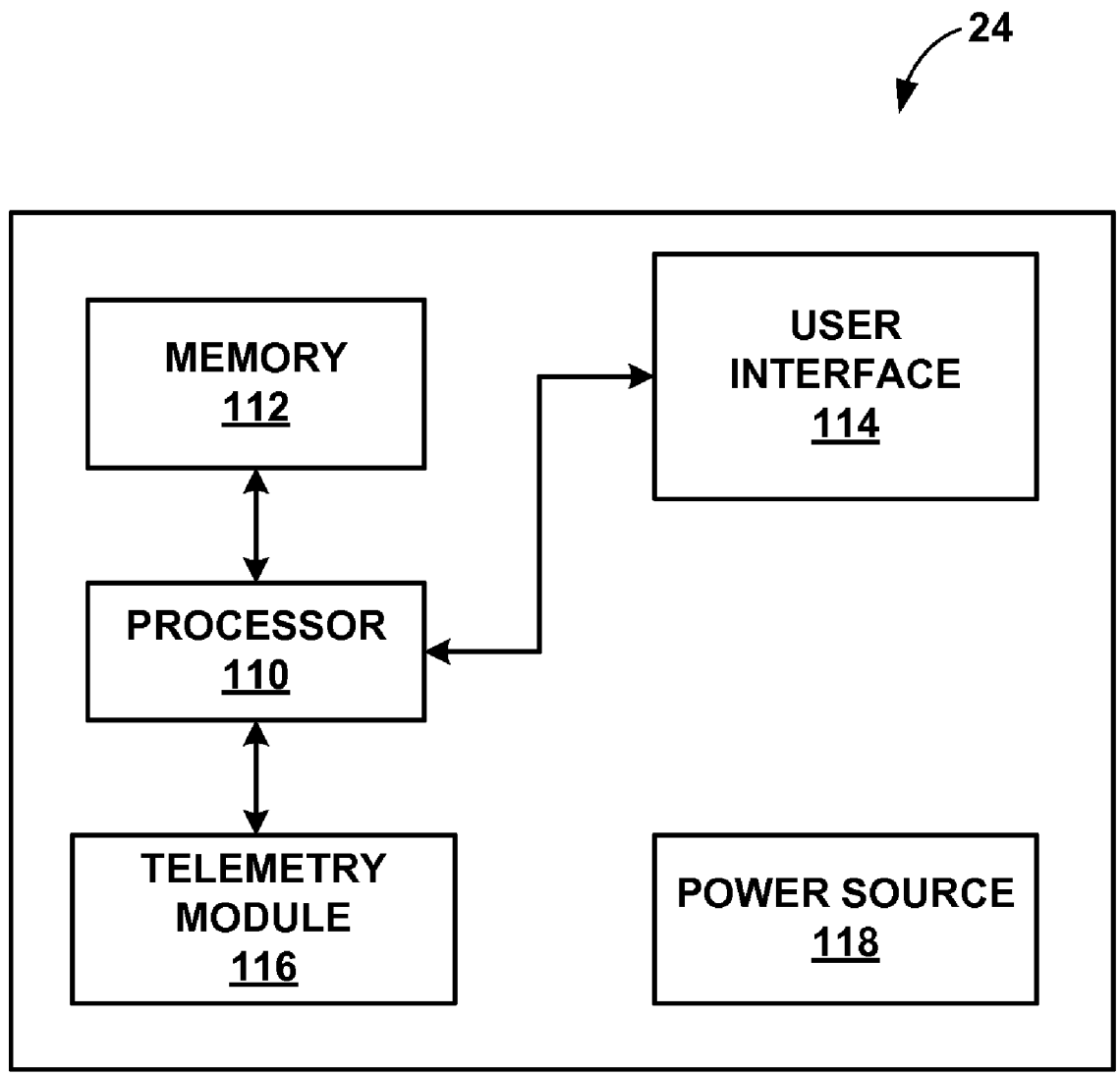
FIG. 6 is a functional block diagram illustrating an example external programmer that facilitates user communication with an IMD.

FIG. 6 is block diagram illustrating an example configuration of programmer 24. As shown in FIG. 6, programmer 24 includes processor 110, memory 112, user interface 114, telemetry module 116, and power source 118. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include display to present graphical user interface to a user, and a keypad or another mechanism for receiving input from a user.

The user may also use programmer 24 to control the pre-qualification of sensing configurations, and any subsequent switching from a primary sensing configuration to an alternate, pre-qualified sensing configuration. Processor 110 may prompt the user for input via user interface 114 before continuing with pre-qualifying or switching sensing configurations. For example, processor 110 and user interface 114 may allow the user to identify the specific sensing configurations to be pre-qualified during the qualification event. User interface 114 may also present stored qualification information, such as a marker channel or other indication of qualification, to a user for selection of an alternate sensing configuration if a sensing integrity condition or other sensing issue with the primary sensing configuration arises.

In some examples, some or all of the functionality ascribed herein to IMD 16 with respect to pre-qualification of sensing configurations may be provided by programmer 24. For example, processor 110 may generate qualification information based on sensed signals received from sensing configurations. Processor 110 may receive such signals from IMD 16 via telemetry module 116. Furthermore memory 112 may store qualification information 92 generated by processor 110 or by processor 80 of IMD 16.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient. Memory 112 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to the programming head that may be placed over heart 12, as described above with reference to FIG. 1. Telemetry module 116 may be similar to telemetry module 88 of IMD 16 (FIG. 4).

Telemetry module 112 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16. In some embodiments, a networked server may generate and store qualification information as described herein with reference to IMD 16 or programmer 24.

Power source 118 delivers operating power to the components of programmer 24. Power source 118 may include a battery and a power generation circuit to produce the operating power. In some embodiments, the battery may be rechargeable to allow extended operation. Recharging may be accomplished by electrically coupling power source 118 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 118 may include circuitry to monitor power remaining within a battery. In this manner, user interface 104 may provide a current battery level indicator or low battery level indicator when the battery needs to be replaced or recharged. In some cases, power source 118 may be capable of estimating the remaining time of operation using the current battery.

Figure 7:
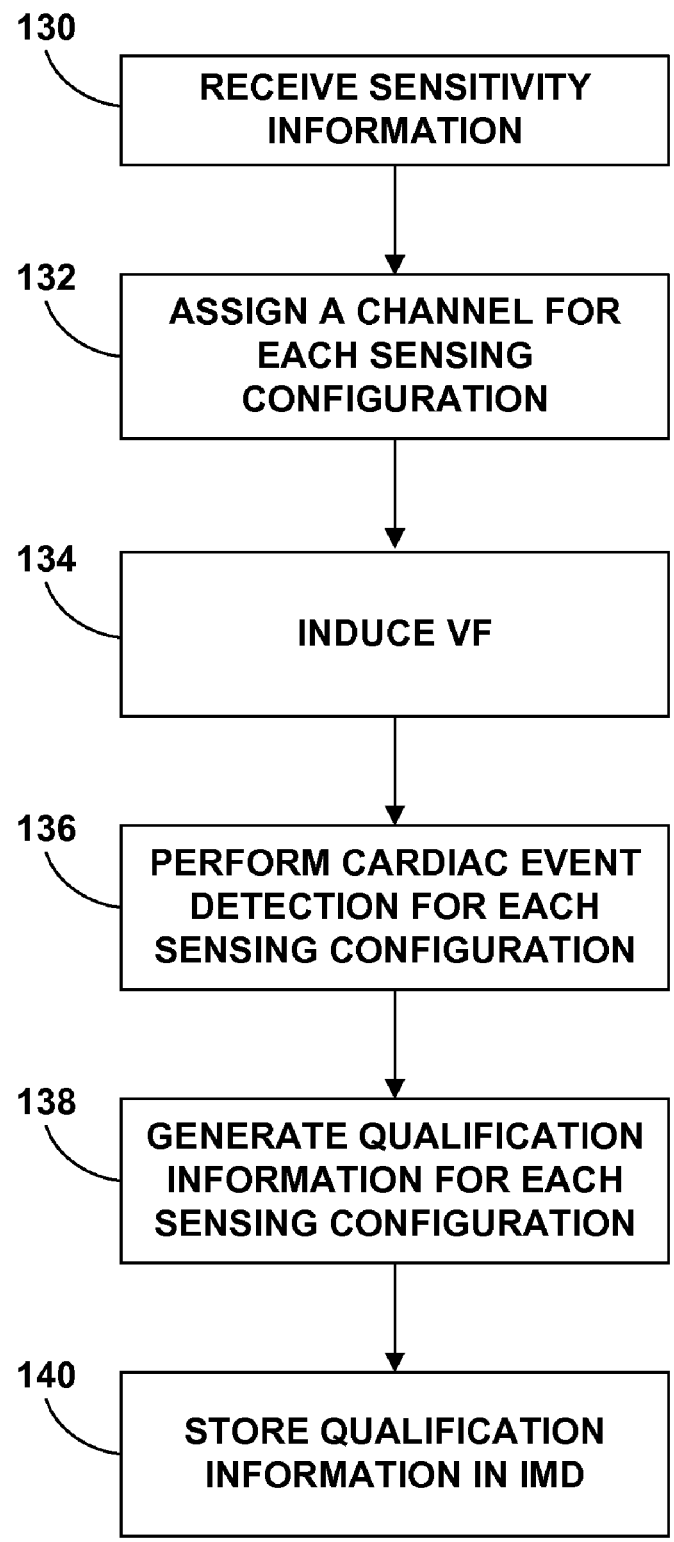
FIG. 7 is a flow diagram illustrating an example technique for pre-qualifying multiple sensing configurations.

FIG. 7 is a flow diagram illustrating an example method for automatically pre-qualifying multiple sensing configurations. Although described with reference to IMD 16, some or all of the example method may be performed by another device, such as programmer 24, a remote server, or another computing device.

Figure 10:
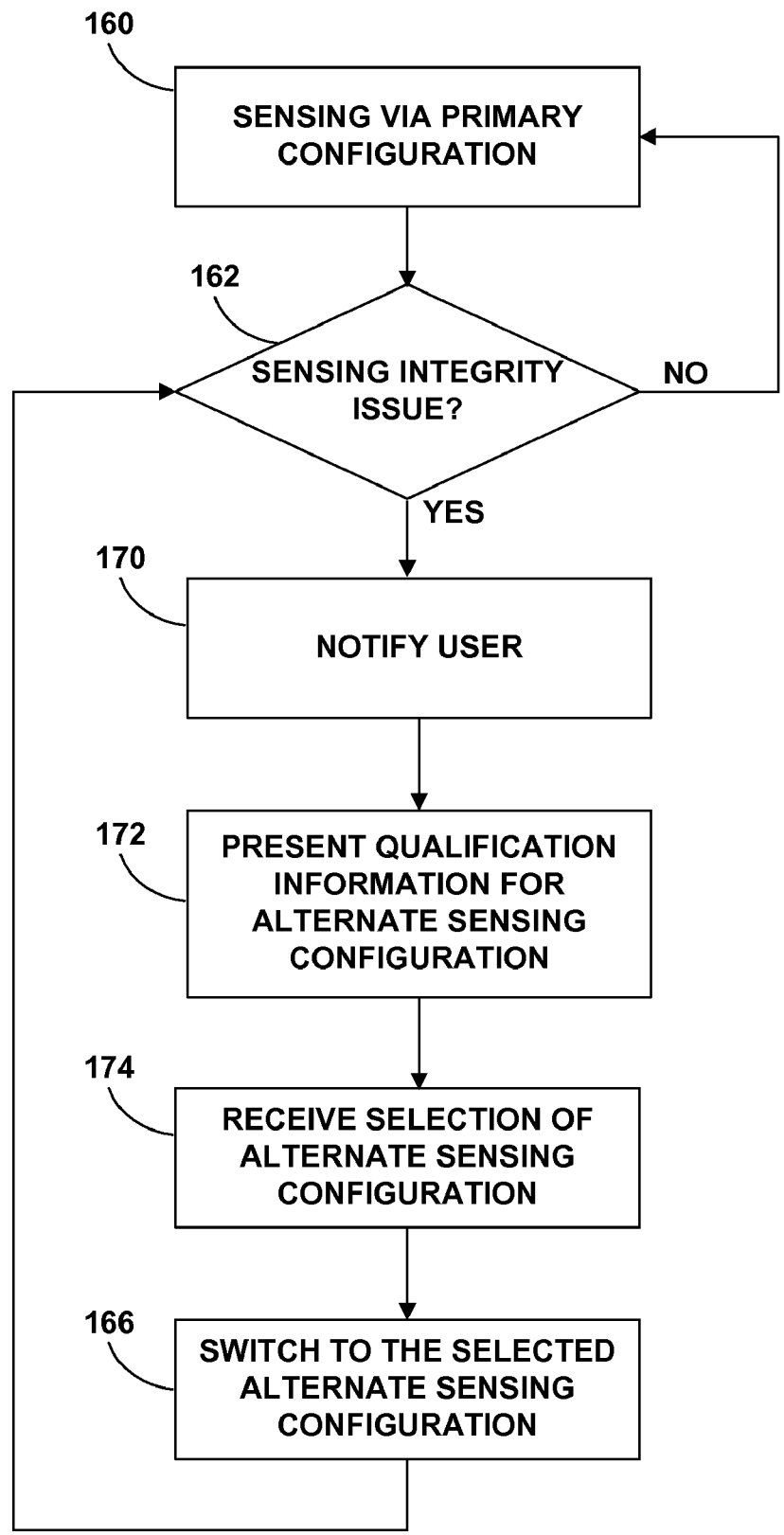
FIG. 10 is a flow diagram illustrating an example technique for user-controlled switching to an alternate pre-qualified sensing configuration.

As shown in FIG. 10, IMD 16 receives sensitivity information regarding the sensitivity at which qualification of sensing configurations should be performed (130). IMD 16 may store sensitivity information in memory 82 or receive the information from programmer 24, e.g., from memory 112 of the programmer or from a value entered by a user of programmer 24. Typically, the qualification sensitivity of the detection channels is set with a safety factor four times greater than that used during chronic monitoring and therapy. For example, the qualification sensitivity may be 1.2 mV, while the normal sensitivity is 0.3 mV.

Next, processor 80 of IMD 16 assigns a respective detection channel from electrical sensing module 86, e.g., a respective narrow band channel 102 or wide band 104, to each sensing configuration to be pre-qualified (132). Processor 80 may determine which sensing configurations should be pre-qualified based upon the types of leads coupled to IMD 16, the number of available detection channels, or any other criteria that may be a factor in the pre-qualification process. Alternatively, processor 80 may receive user selection of sensing configurations for pre-qualification via programmer 24 and telemetry module 88.

According to the example method illustrated in FIG. 7, IMD 16 also induces a tachyarrhythmia, e.g., ventricular fibrillation (VF), of heart 12 of patient 14 (134). For example, processor 80 may control signal generator 84 to deliver a signal via at least some of electrodes 40, 42, 44, 46, 48, 50, 62, 64 and 66 to induce the tachyarrhythmia. Processor 80 may control the induction of the tachyarrhythmia under the control of a clinician, e.g., based on signals received from programmer 24 via telemetry module 88.

IMD 16 performs cardiac event detection on the signals sensed by each sensing configuration (136). For example, narrow band detection channels 102 may detect cardiac events in signals sensed by sensing configurations coupled thereto, and provide indications of the detected cardiac events to processor 80. As another example, processor 80 may analyze signals received from wide band channels 104 to detect cardiac events.

Processor 80 may then generate qualification information 92 for each of the sensing configurations (138) that indicates an accuracy of the cardiac event detection via the sensing configuration. The qualification information may include which sensing configurations accurately detected the ventricular fibrillation event and is now pre-qualified, which sensing configurations did not detect accurately detect the fibrillation, and any sensitivity or setting information for a pre-qualified sensing configuration. Processor 80 may store the qualification information 92 within memory 82 of IMD 16, or a memory of another device (140). Processor 80 may also select the primary sensing configuration, and in some cases may select the primary sensing configuration based on the qualification information.

Figure 8:
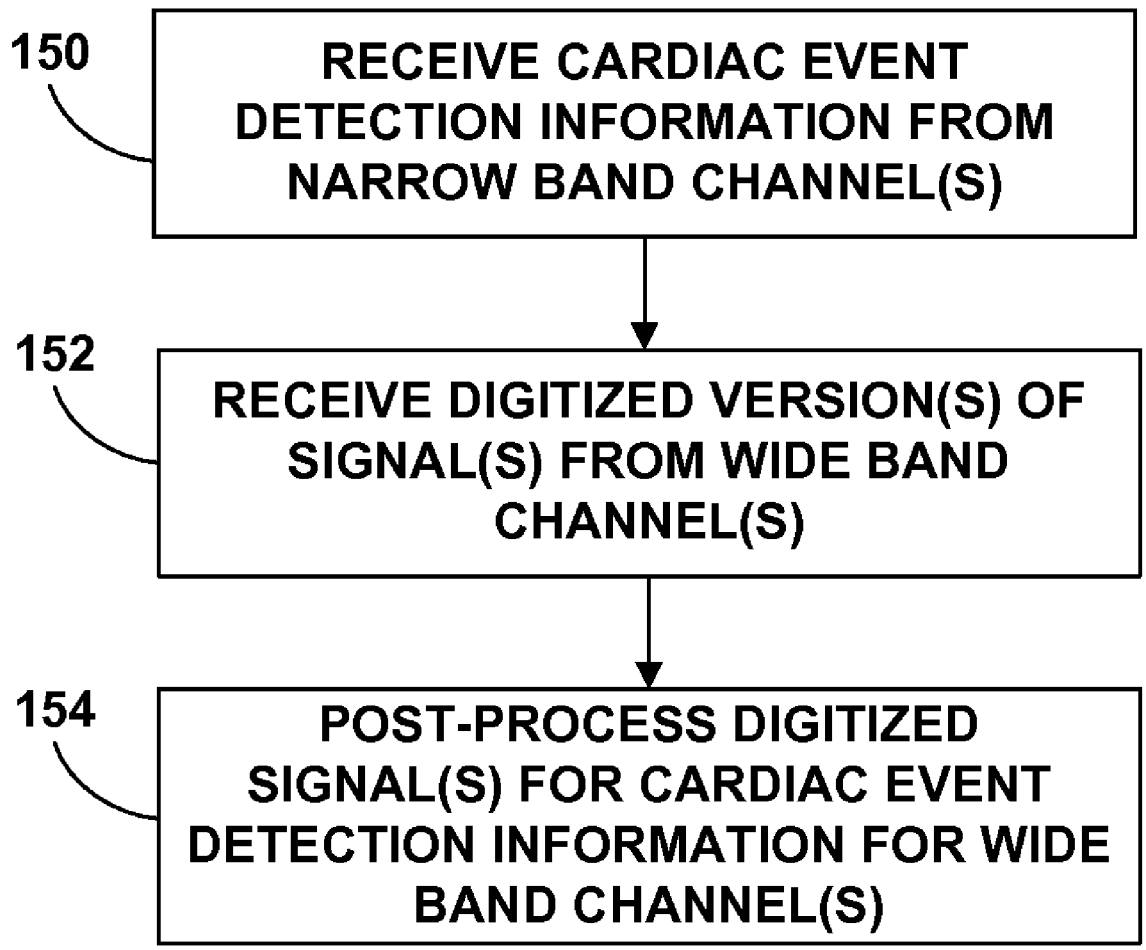
FIG. 8 is a flow diagram illustrating an example technique for generating qualification information for a plurality of sensing configurations.

FIG. 8 is a flow diagram illustrating an example technique for generating qualification information for a plurality of sensing configurations. The example technique of FIG. 8 is described as being performed by processor 80 of IMD 16. In other examples, the example technique of FIG. 8 may be performed by processor 110 of programmer 24, or another processor or device.

As shown in FIG. 8, processor 80 receives cardiac event detection information, e.g., signals indicating the occurrence of cardiac events, from one or more narrow band channels 102 (150). Processor 80 further receives one or more digitized versions of signals received by one or more wide band channels 104 from ADC 108 (152). Processor 80 may store the digitized signals in memory 82, and may post-process, e.g., after the induced fibrillation is terminated or otherwise after the qualification event, the digitized signal to detect cardiac events within the signal (154). Processor 80 may also process the digitized signals from one channel in real-time while post-processing additional digitized signals to generate multiple pre-qualified sensing configurations. As discussed above, in some examples, processor 80 may process a single channel, e.g., a narrow-band channel 102, in real time, and post-process one or more additional narrow or wide band channels.

Figure 9:
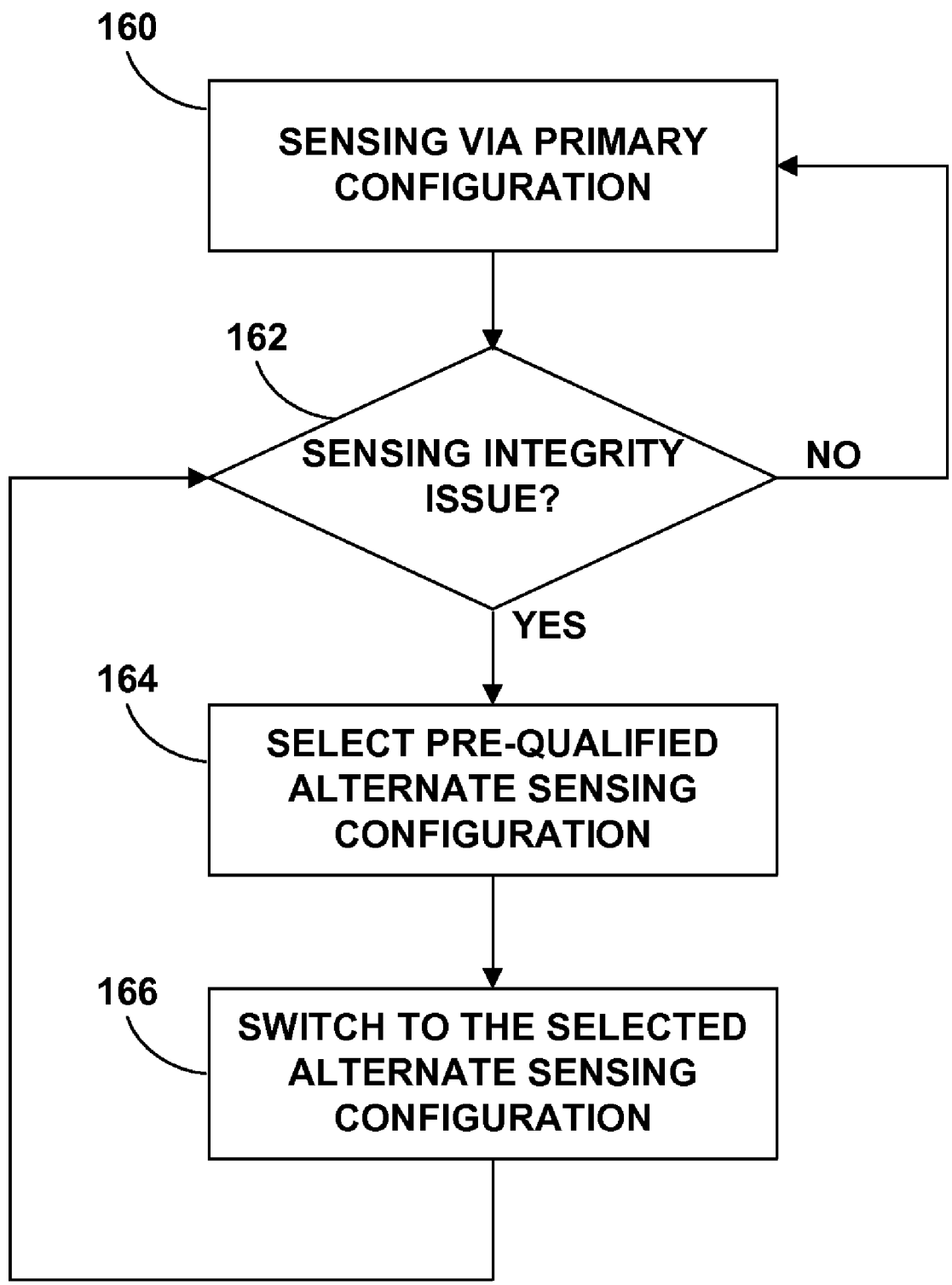
FIG. 9 is a flow diagram illustrating an example technique for automatically switching to an alternate pre-qualified sensing configuration.

FIG. 9 is a flow diagram illustrating an example method for switching to an alternate pre-qualified sensing configuration during therapy. The example technique of FIG. 9 is described as being performed by processor 80 of IMD 16. In other examples, the example technique of FIG. 9 may be performed by processor 110 of programmer 24, or another processor or device.

As shown in FIG. 9, processor 80 initially controls sensing module 86 to sense cardiac events via a primary sensing configuration (160). Processor 80 also monitors or periodically checks for any sensing integrity issue with the current (primary) sensing configuration (162). If processor 80 identifies a sensing integrity issue (162), then processor 80 selects a pre-qualified alternate sensing configuration (164), and switches to the selected sensing configuration (166), e.g., controls sensing module 86 to sense via the alternate configuration by coupling a detection channel of the sensing module to the alternate configuration. Processor 80 may continue to monitor for sensing integrity issues with the alternate sensing configuration (162).

FIG. 10 is a flow diagram illustrating an example technique for user-controlled switching to an alternate pre-qualified sensing configuration. The example technique of FIG. 10 is described as being performed by processor 80 of IMD 16. In other examples, the example technique of FIG. 10 may be performed by processor 110 of programmer 24, or another processor or device.

Processor 80 controls sensing via the primary configuration (160) and monitors or checks for an integrity issue (162) as described above with respect to FIG. 9. If processor 80 identifies a sensing integrity issue, processor 80 notifies a user (170). For example, processor 80 may provide an indication of the sensing integrity issue to programmer 24 or a remote server via telemetry module 88 for communication to the user. Processor 80 may also present qualification information 92 for one or more alternate sensing configurations to the user, e.g., via programmer 24 or a server (172). Processor 80 may receive a user selection of an alternate sensing configuration, or confirmation of an alternate configuration selected by processor 80 (174), and control switching to the alternate configuration (166).

Figure 11:
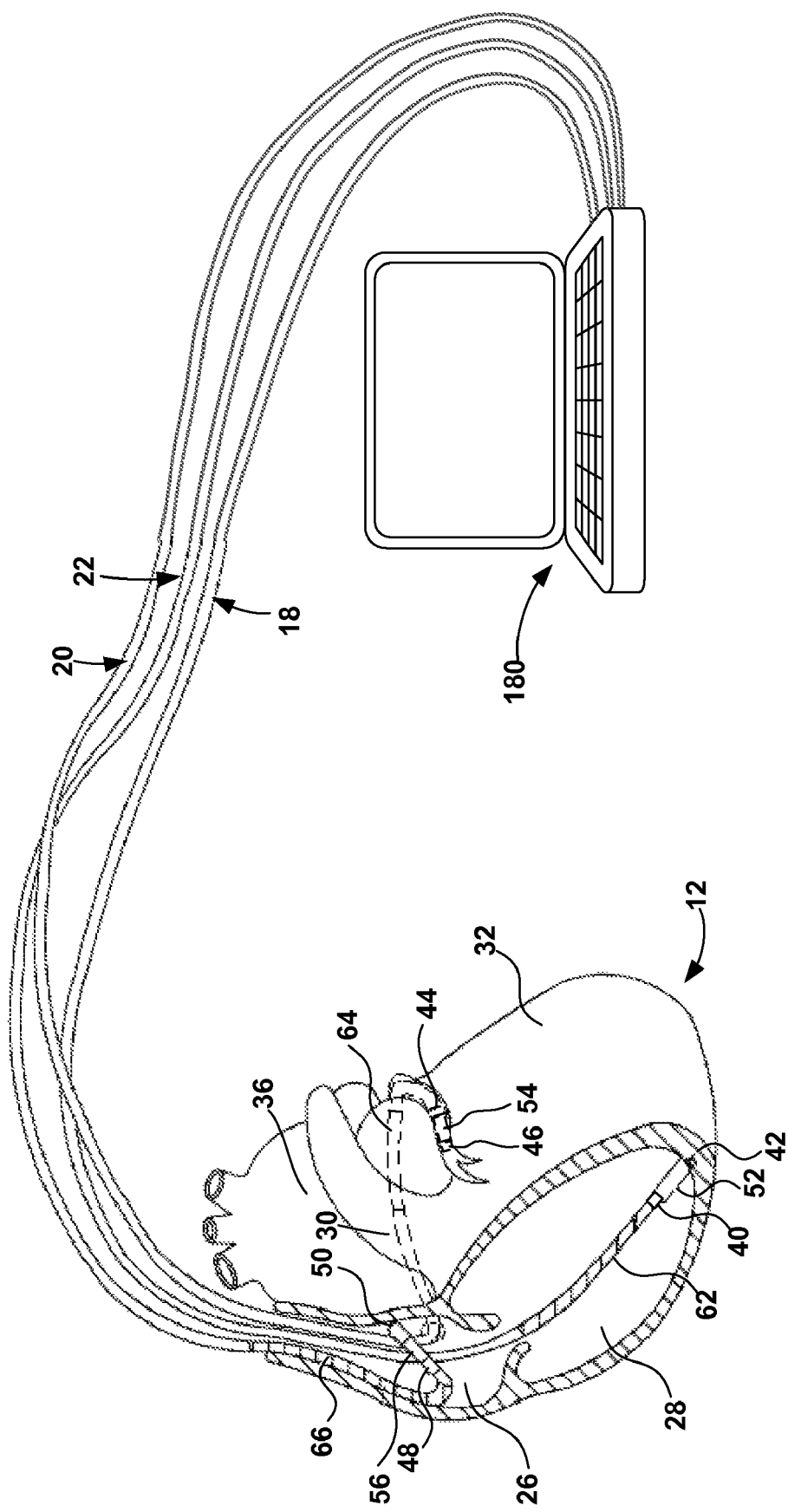
FIG. 11 is a conceptual diagram illustrating the leads of the therapy system of FIG. 1 coupled to an example analyzer used to test the leads and perform cardiac signal assessment during lead implantation.

FIG. 11 is a conceptual diagram illustrating leads 18, 20 and 22 of therapy system 10 coupled to an example analyzer 180 used to test the leads and perform cardiac signal assessment during lead implantation. After leads 18, 20, 22 are implanted in patient 14, the clinician may desire to assess the leads and patient 14 condition prior to coupling the leads to IMD 16 and implanting the IMD. Analyzer 180 may use test signals to generate lead integrity information and lead performance information that could indicate potential problems with any of leads 18, 20, 22 that could be corrected prior to completing implantation of leads and IMD 16.

After leads 18, 20, 22 are determined to be operational, analyzer 180 may assess certain conditions of the heart. For example, analyzer 180 may perform a sinus rhythm assessment to identify the dynamics of the atrial signals from the sinoatrial node as an indication of heart electrical function. The sinus rhythm assessment may also identify whether a sensing configuration will be susceptible to oversensing, such as T-wave oversensing. A qualification event for qualifying a plurality of sensing configurations may include a sinus rhythm assessment instead of or in addition to a tachyarrhythmia induction. Analyzer 180 may include a processor and memory substantially similar to IMD 16 and/or programmer 24, and perform the functions with respect to pre-qualifying sensing configurations ascribed herein to the IMD and programmer.

Alternatively, pre-qualifying sensing configurations may be performed during any ambulatory heart rhythm. For example, the qualification event may include pacing, atrial fibrillation, spontaneous ventricular tachycardia, supraventricular tachycardia, or any other detected heart rhythm. In this manner, pre-qualification may be performed during any cycle of heart 12, depending upon the implementation of the stimulation therapy.

Figure 12A:
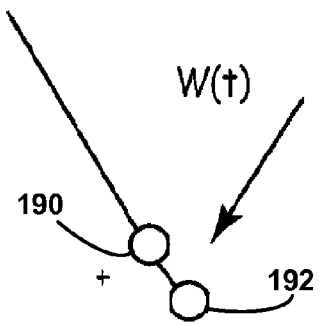
FIGS. 12A and 12B are diagrams illustrating differences in susceptibility to differential filtering to a wavefront between true bipolar and integrated bipolar electrode sensing configurations.
Figure 12B:
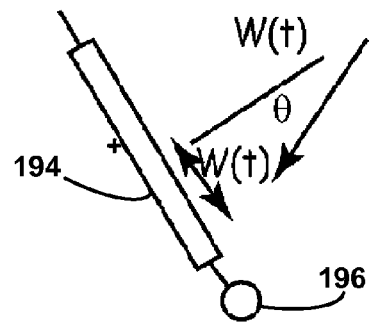

FIGS. 12A and 12B are diagrams illustrating differences in susceptibility to differential filtering to a wavefront between true bipolar and integrated bipolar electrode sensing configurations. Alternate sensing configurations may need to be pre-qualified differently because of differences in detecting ventricular fibrillations. True bipolar sensing may be more susceptible to differential elimination of signals moving in a direction orthogonal to the bipole formed by tip electrode 192, similar to electrodes 42, 46 and 50, and ring electrode 190, similar to electrodes 40, 44 and 48. Integrated bipolar sensing between tip electrode 196, similar to electrodes 42, 46 and 50, and coil electrode 194, similar to elongated electrodes 62, 64 and 66, is inherently less susceptible to differential elimination due to the difference in size of the two electrodes.

FIGS. 12A and 12B demonstrate a situation where differential elimination is more complete with a true bipolar sensing configuration versus an integrated bipolar sensing configuration. In this representation, a wavefront represented by vector W(T) is shown moving nearly perpendicular to a true bipolar (TB) sensing configuration in FIG. 12A and an integrated bipolar (IB) sensing configuration in FIG. 12B. The resulting signal with the true bipolar configuration is likely to be near zero since electrodes 190 and 192 are closely spaced and of substantially the same size, and the wavefront will tend to reach both electrodes at about the same time. With the integrated bipolar sensing configuration of FIG. 12B, the wavefront will vary according to the projection of W(T) according to $\cos \Theta$, where $\Theta$ is the angle between normal to coil electrode 194 and the direction of vector W(T). Therefore, each desired sensing configuration may be pre-qualified in order to know if an alternate sensing configuration will be able to accurately detect cardiac events, e.g., depolarizations. Furthermore, a sinus rhythm assessment may be able to identify oversensing or undersensing for such configurations.

Figure 13:
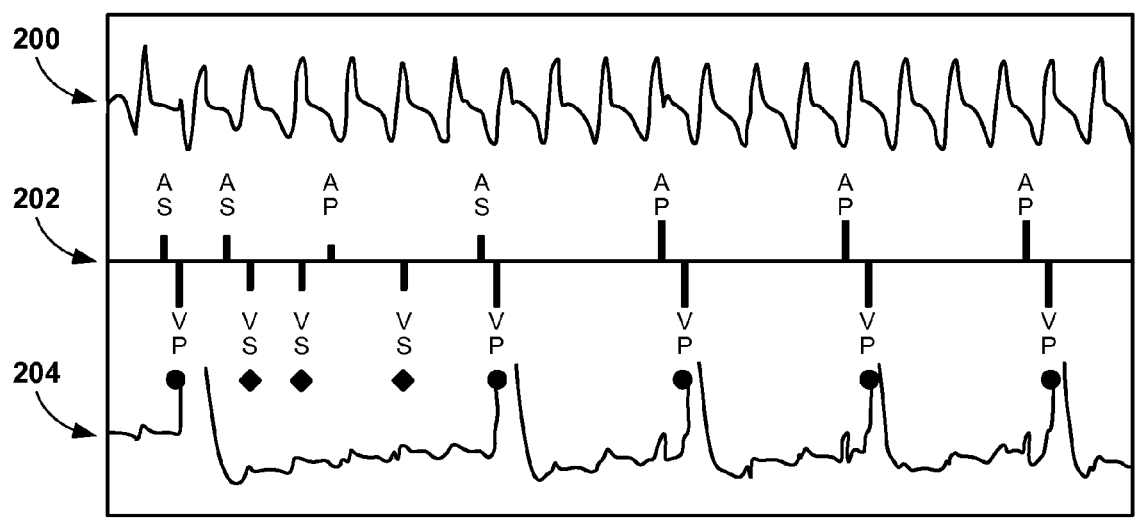
FIG. 13 is a graph illustrating an example of R-wave undersensing by a true bipolar electrode sensing configuration.

FIG. 13 is a graph illustrating an example of R-wave undersensing by a true bipolar electrode sensing configuration in the case of a ventricular tachycardia having a right bundle branch block (RBBB) activation pattern. The following description illustrates an advantage to pre-qualifying additional sensing configurations. Top trace 200 is an electrocardiogram (ECG) pattern. Center trace 202 is a marker channel showing atrial sense events and ventricular sense events. The ventricular sense events were based upon signal processing of the true bipolar EGM sensor signal shown in bottom trace 204. A comparison of the ECG pattern 200 with traces 202 and 204 shows that only a fraction of the R-waves were sensed.

Oversensing and undersensing for a plurality of sensing configurations may be evaluated during a qualification event. Furthermore, oversensing and undersensing may be evaluated for a current, e.g., primary, sensing configuration, in order identify any sensing integrity issue with current sensing configuration. A signal from a sensing configuration may analyzed by processor 80 to see whether a cardiac event rate is higher and due to known sources of oversensing, such as P-wave oversensing, T-wave oversensing, R-wave double counting, lead fracture/insulation breaks, EMI, or muscle noise. The analyses may include checking for evidence of simultaneous sensing of both the atrial sensing and the ventricular sensing indicating P-wave oversensing, and the use of morphology analysis and comparison of stability of adjacent beats to identify T-wave oversensing. Other sources of noise can be detected using a short interval counter to identify intervals that are too short to have been produced by physiologic sources.

Figure 14:
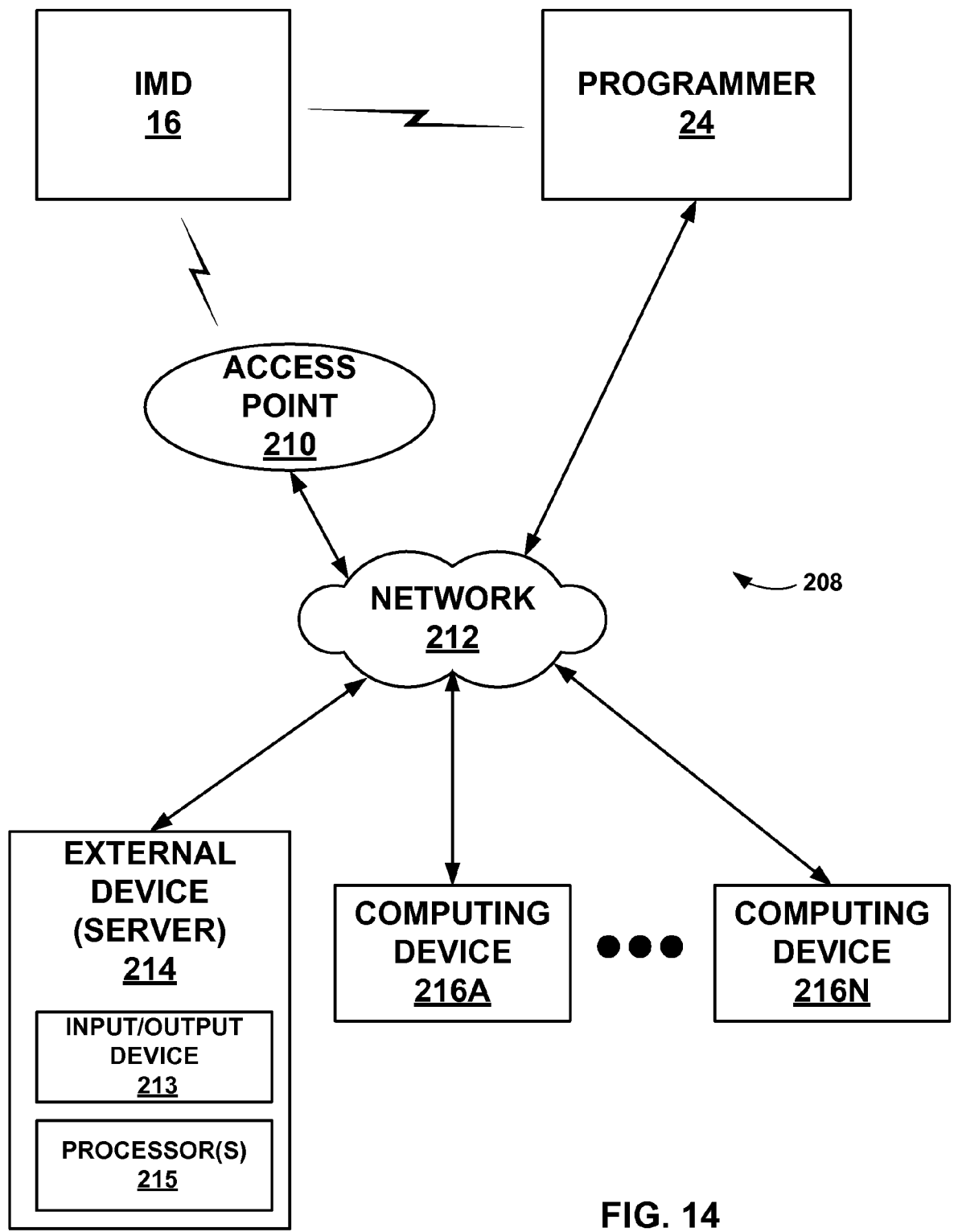
FIG. 14 is a block diagram illustrating an example system that includes an external device, such as a server, and one or more computing devices that are coupled to the IMD and programmer shown in FIG. 1 via a network.

FIG. 14 is a block diagram illustrating an example system 208 that includes an external device, such as a server 214, and one or more computing devices 216A-216N, that are coupled to the IMD 16 and programmer 24 shown in FIG. 1 via a network 212. In this example, IMD 16 may use its telemetry module 88 to communicate with programmer 24 via a first wireless connection, and to communication with an access point 210 via a second wireless connection. In the example of FIG. 14, access point 210, programmer 24, server 214, and computing devices 216A-216N are interconnected, and able to communicate with each other, through network 212. In some cases, one or more of access point 210, programmer 24, server 214, and computing devices 216A-216N may be coupled to network 212 through one or more wireless connections. IMD 16, programmer 24, server 214, and computing devices 216A-216N may each comprise one or more processors, such as one or more microprocessors, DSPs, ASICs, FPGAs, programmable logic circuitry, or the like, that may perform various functions and operations, such as those described herein. For example, as illustrated in FIG. 14, server 214 may comprise one or more processors 215 and an input/output device, which need not be co-located.

Server 214 may, for example, generate qualification information 92 based on sensed signals for a plurality of sensing configurations received from IMD 16 via network 212. Server 214 may include a memory to store qualification information 92 received from IMD 16 via network 212. As another example, server 214 may generate web-pages to serve qualification information 92 to computing devices 216 for viewing by clinicians or other users. In this manner, qualification information 92 may be distributed over network 212 in order for a clinician or technician can review each possible sensing configuration. Remote pre-qualification of sensing configurations are possible by utilizing network 212. In addition, network 212 may be used for a clinician to switch to a pre-qualified sensing configuration if a sensing integrity condition arises with the primary sensing configuration.

Access point 210 may comprise a device that connects to network 212 via any of a variety of connections, such as telephone dial-up, digital subscriber line (DSL), or cable modem connections. In other embodiments, access point 210 may be coupled to network 212 through different forms of connections, including wired or wireless connections. Network 212 may comprise a local area network, wide area network, or global network, such as the Internet. System 208 may be implemented, in some aspects, with general network technology and functionality similar to that provided by the Medtronic CareLink® Network developed by Medtronic, Inc., of Minneapolis, Minn.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various additional examples and techniques may be derived from this disclosure. For example, the pre-qualified sensing configurations are not limited to electrodes, or electrodes detecting cardiac events. Instead of or in addition to sensing vectors comprising two or more electrodes for sensing cardiac events, sensing configurations may include other sensors located along leads 18, 20, and 22, on or within IMD 16, elsewhere within patient 12, or external to patient 12. Thus, in some examples, a system or device that generates qualification information according to this disclosure may include one or more sensors that generate a signal as a function of a physiological parameter of a patient.

Such sensors may include activity sensors, posture sensors, pressure sensors, respiration sensors, oxygen saturation sensors, impedance sensors, or the like. In some examples, these sensors may comprise electrodes located on leads 18, 20 and 22, or on IMD 16. In some examples, electrodes used to sense cardiac events may additionally be used to detect other physiological parameters, such as impedance or respiration. A sensing configuration may comprise either or both of an electrode configuration for cardiac event sensing or another physiological sensor. These and other examples are within the scope of the disclosure.

The invention claimed is:

1. A method comprising:
receiving a plurality of sensed signals, each of the sensed signals sensed by a respective one of a plurality of sensing configurations during a qualification event;
analyzing each of the sensed signals to detect cardiac events during the qualification event;
generating qualification information for each of the sensing configurations based on the analysis, the qualification information for each of the sensing configurations indicating whether the sensing configuration is qualified for subsequent cardiac event detection based on an accuracy of the cardiac event detection for that sensing configuration during the qualification event;
identifying a first qualified one of the plurality of sensing configurations as a primary sensing configuration and a second qualified one of the plurality of sensing configurations as an alternate sensing configuration;
storing the qualification information for at least the alternate sensing configuration; and
receiving a signal sensed by the primary sensing configuration subsequent to the qualification event;
analyzing the signal received subsequent to the qualification event to detect cardiac events subsequent to the qualification event; and
subsequently switching, based on the previously stored qualification information for the alternate sensing configuration, from receiving and analyzing the signal sensed by the primary sensing configuration to receiving and analyzing a signal sensed by the alternate sensing configuration to detect cardiac events.

2. The method of claim 1, wherein each of the sensing configurations comprises a respective one of a plurality of different combinations of two or more electrodes from a plurality of electrodes implanted within a patient.

3. The method of claim 1, further comprising inducing a tachyarrhythmia during an implantation procedure that includes implanting an implantable medical device within the patient subsequent to the implantation, wherein the qualification event comprises the tachyarrhythmia induction.

4. The method of claim 1, wherein storing the qualification information comprises storing the qualification information within an implantable medical device.

5. The method of claim 1,
further comprising identifying a sensing integrity condition affecting the primary sensing configuration,
wherein subsequently switching from receiving and analyzing the signal sensed by the primary sensing configuration to receiving and analyzing the signal sensed by the alternate sensing configuration comprises switching from the primary sensing configuration to the alternate sensing configuration in response to the identification of the sensing integrity condition affecting the primary sensing configuration.

6. The method of claim 5, wherein switching from the primary sensing configuration to the alternate sensing configuration comprises:
presenting the stored qualification information for the alternate sensing configuration to a user in response to the identification of the sensing integrity condition affecting the primary sensing configuration;
receiving switching input from the user; and
switching from the primary sensing configuration to the alternate sensing configuration in response to the switching input.

7. The method of claim 5, wherein switching from the primary sensing configuration to the alternate sensing configuration comprises automatically switching from the primary sensing configuration to the alternate sensing configuration.

8. The method of claim 1, wherein the qualification information for the alternate sensing configuration comprises a marker channel for the alternate sensing configuration.

9. The method of claim 1, wherein analyzing each of the sensed signals comprises:
analyzing at least one of the signals substantially in real-time; and
storing and subsequently analyzing at least one other of the signals.

10. The method of claim 1, wherein the qualification event comprises a sinus rhythm assessment, and analyzing each of the sensed signals to detect cardiac events during the qualification event comprises analyzing each of the sensed signals to detect at least one of oversensing or undersensing of cardiac events.

11. The method of claim 1, wherein at least one of the sensing configurations comprises a physiological parameter sensor.

12. A method comprising:
receiving a plurality of sensed signals, each of the sensed signals sensed by a respective one of a plurality of sensing configurations during a qualification event;
analyzing each of the sensed signals to detect cardiac events during the qualification event; and
generating qualification information for each of the sensing configurations based on the analysis, the qualification information for each of the sensing configurations indicating whether the sensing configuration is qualified for subsequent cardiac event detection based on an accuracy of the cardiac event detection for that sensing configuration during the qualification event,
wherein receiving a plurality of sensed signals comprises:
receiving at least one of the signals with a narrow band filtered sense-amplifier; and
receiving at least one other of the signals with a wide band filtered sense-amplifier.

13. A system comprising:
a sensing module that receives a plurality of sensed signals, each of the sensed signals sensed by a respective one of a plurality of sensing configurations during a qualification event;
a processor that controls coupling of the sensing configurations to the sensing module; and
a memory,
wherein at least one of the sensing module and the processor analyzes each of the sensed signals to detect cardiac events during the qualification event,
wherein the processor generates qualification information for each of the sensing configurations based on the analysis, the qualification information for each of the sensing configurations indicating whether the sensing configuration is qualified for subsequent cardiac event detection based on an accuracy of the cardiac event detection for the sensing configuration during the qualification event,
wherein the processor identifies a first qualified one of the plurality of sensing configurations as a primary sensing configuration for subsequent cardiac event detection and a second qualified one of the plurality of sensing configurations as an alternate sensing configuration, controls subsequent cardiac event detection by the sensing module via the primary sensing configuration, and stores the qualification information for at least the alternate sensing configuration within the memory, and
wherein the processor subsequently switches the sensing module from the primary sensing configuration to the alternate sensing configuration for cardiac event detection based on the qualification information for the alternate sensing configuration previously stored within the memory.

14. The system of claim 13, further comprising a plurality of electrodes implanted within a patient, wherein each of the sensing configurations comprising a respective one of a plurality of different combinations of two or more electrodes from the plurality of electrodes.

15. The system of claim 14,
further comprising a signal generator,
wherein the processor controls the signal generator to deliver electrical stimulation to the patient via at least some of the electrodes to induces a tachyarrhythmia during an implantation procedure that includes implanting the plurality of electrodes within the patient subsequent to the implantation of the electrodes, and wherein the qualification event comprises the tachyarrhythmia induction.

16. The system of claim 14, further comprising
an external analyzer coupled to the plurality of electrodes, wherein the external analyzer comprises the sensing module and the processor,
wherein the qualification event comprises a sinus rhythm assessment,
wherein at least one of the sensing module or the processor analyzes each of the sensed signals to detect at least one of oversensing or undersensing of cardiac events.

17. The system of claim 13, further comprising an implantable medical device, wherein the implantable medical device comprises the memory.

18. The system of claim 13, wherein the processor identifies a sensing integrity condition affecting the primary sensing configuration, and switches cardiac event detection by the sensing module from the primary sensing configuration to the alternate sensing configuration in response to the identification of the sensing integrity condition affecting the primary sensing configuration.

19. The system of claim 18, wherein the processor identifies the sensing integrity condition based on at least one of oversensing of cardiac events, undersensing of cardiac events, or a lead integrity condition.

20. The system of claim 18, further comprising a user interface that presents the stored qualification information for the alternate sensing configuration to a user in response to the identification of the sensing integrity condition affecting the primary sensing configuration, and receives switching input from the user, wherein the processor switches cardiac event detection by the sensing module from the primary sensing configuration to the alternate sensing configuration in response to the switching input.

21. The system of claim 13, wherein the qualification information for the alternate sensing configuration comprises a marker channel for the alternate sensing configuration.

22. The system of claim 13, further comprimising an implantable medical device, wherein the implantable medical device comprises the sensing module and the processor.

23. The system of claim 22, wherein the implantable medical device comprises and implantable pacemaker-cardioverter-defribrillator.

24. The system of claim 13, further comprising at least one physiological parameter sensor coupled to the sensing module, wherein at least one of the sensing configurations comprises the physiological parameter sensor.

25. A system comprising:
a plurality of electrodes implanted within a patient
a sensing module that receives a plurality of sensed signals, each of the sensed signals sensed by a respective one of a plurality of sensing configurations during a qualification event, wherein each of the sensing configurations comprises a respective one of a plurality of different combinations of two or more electrodes from the plurality of electrodes;
a processor that controls coupling of the sensing configurations to the sensing module; and
a memory,
wherein at least one of the sensing module and the processor analyzes each of the sensed signals to detect cardiac events during the qualification event,
wherein the processor generates qualification information for each of the sensing configurations based on the analysis, the qualification information for each of the sensing configurations indicating whether the sensing configuration is qualified for subsequent cardiac event detection based on an accuracy of the cardiac event detection for the sensing configuration during the qualification event,
wherein the sensing module comprises at least one narrow band filtered sense-amplifier that receives at least one of the sensed signals and at least one wide band filtered sense-amplifier that receives at least one other of the sensed signals,
wherein the sensing module analyzes the sensed signal received by the narrow band filtered sense-amplifier with the narrow band filtered sense-amplifier substantially in real-time, and
wherein the processor converts the sensed signal received by the wide band filtered sense-amplifier to a digital signal, stores the signal within the memory, and subsequently analyzes the digital signal to detect cardiac events that occurred during the qualification event.

26. A system comprising:
means for receiving a plurality of sensed signals, each of the sensed signals sensed by a respective one of a plurality of sensing configurations during a qualification event;
means for analyzing each of the sensed signals to detect cardiac events during the qualification event;
means for generating qualification information for each of the sensing configurations based on the analysis, the qualification information for each of the sensing configurations indicating whether the sensing configuration is qualified for subsequent cardiac event detection based on an accuracy of the cardiac event detection for the sensing configuration during the qualification event;
means for identifying a first qualified one of the plurality of sensing configurations as a primary sensing configuration and a second qualified one of the plurality of sensing configurations as an alternate sensing configuration; and
means for storing the qualification information for at least the alternate sensing configuration,
wherein the means for receiving receives a signal sensed by the primary sensing configuration subsequent to the qualification event and the means for analyzing analyzes the signal sensed by the primary sensing configuration subsequent to the qualification event to detect cardiac events subsequent to the qualification event,
the system further comprising means for subsequently switching, based upon the previously stored qualification information for the alternate sensing configuration, the means for receiving and the means for analyzing from the primary sensing configuration to the alternate sensing configuration to detect cardiac events.

* * * * *